US006884629B2

(12) United States Patent
Gore et al.

(10) Patent No.: US 6,884,629 B2
(45) Date of Patent: Apr. 26, 2005

(54) IMMUNOGLOBULIN BINDING PROTEIN

(75) Inventors: Michael Graham Gore, Southhampton (GB); Jennifer Ann Beckingham, Ann Arbour (GB); Sian Eleri Roberts, Wiltshire (GB)

(73) Assignee: Affitech AS, Oslo (NO)

( * ) Notice: Subject to any disclaimer, the term of this patent is extended or adjusted under 35 U.S.C. 154(b) by 127 days.

(21) Appl. No.: 09/808,212

(22) Filed: Mar. 13, 2001

(65) Prior Publication Data

US 2002/0137918 A1 Sep. 26, 2002

Related U.S. Application Data

(63) Continuation of application No. PCT/GB99/03048, filed on Sep. 14, 1999.

(30) Foreign Application Priority Data

Sep. 14, 1998 (GB) .............................. 9819998
Apr. 26, 1999 (GB) .............................. 9909578

(51) Int. Cl.$^7$ ............................... G01N 33/53
(52) U.S. Cl. ................. 436/547; 530/413; 435/7.1; 435/7.92
(58) Field of Search ................ 435/7.1, 7.92; 530/413; 436/54

(56) References Cited

U.S. PATENT DOCUMENTS 6,162,903 A * 12/2000 Trowern et al. ....... 530/388.25

FOREIGN PATENT DOCUMENTS

| WO | WO 93/22342 | 11/1993 |
| WO | WO 93/22439 | 11/1993 |

OTHER PUBLICATIONS

Beckingham et al., "Interactions Between a Single Immunoglobulin–Binding Domain of Protein L from Peptostreptococcus Magnus and a Human κ Light Chain," *Biochem J.* 340(Pt 1):193–199, May 15, 1999.
Bottomley et al., "Cloning, Expression and Purification of *Ppl*–1, a Kappa–Chain Binding Protein, Based Upon Protein L from Peptostreptococcus Magnus," *Bioseparation* 5:359–367, 1995.
Wikström et al., "Mapping of the Immunoglobulin Light Chain–Binding Site of Protein L," *J. Mol. Biol.* 250:128–133, 1995.
Akerstrom, Bo et al., Protein L: An Immunoglobuulin Light Chain –binding Bacterial Protein, J Biol. Chem., Nov. 25, 2989, vol. 264, pp. 19740–19746.
Beckingham, Jennifer A. et al., Equilibrium and Pre–equilibrium Fluorescence Studies on the Interaction between Protein L and Kappa Light Chain, UK Biochemical Society, 38S Biochemical Society Transactions (1997) 25.

Bjorck, Lars, Protein L –A Novel Bacterial Cell Wall Protein with Affinity for Ig L Chains, The Journal of Immunology, Feb. 15, 1988, vol. 140, No. 4, pp. 1194–1197.
Enokizono, Junichi et al. NMR Analysis of the Interaction between Protein L and Ig Light Chains, J. Mol. Biol., 1997, vol. 270, pp. 8–13.
Goward, Christopher R. et al., Molecular Evolution of Bacterial Cell–surface Proteins, TIBS, Apr. 1993, pp. 136–140.
Kastern, William et al., Protein L: A Bacterail Immunoglobulin–binding Protein and Possible Virulence Determinant, Infection and Immunology, May 1990, pp. 1217–1222.
Kastern, William et al., Structure of Peptostreptococcal Protein L and Identification of a Repeated Immunoglobulin Light Chain–binding Domain, J. Biol. Chem., Jun. 25, 1992, vol. 267, No. 18, pp. 12820–12825.
Kihlberg, Britt–Marie et al., Protein LG: A Hybrid Molecule with Unique Immunoglobulin Binding Properties, J. Biol. Chem., Dec. 15, 1992, vol. 267, No. 25, pp. 25583–25588.
Kihlberg, Britt–Marie et al., Characterization of the Binding Properties of Protein LG, an Immunoglobulin–binding Hybrid Protein, 1996, Eur. J. Biochem. vol. 240, pp. 556–563.
Kim, David E. et al., The Single Helix in Protein L is Largely Disrupted at the Rate–limiting Step in Folding, 1998, J. Mol. Biol., vol. 284, pp. 807–815.
Murphy, Jonathan P. et al., The Functional Units of a Peptostreptococcal Protein L, 1994, Molecular Microrbiology vol. 12, No. 6, pp. 911–920.
Myhre, Erling B. and Erntell, Mats, A Non–immune Interaction Between the Light Chain of Human Immunoglobulin and a Surface Component of a Peptococcus Magnus Strain, Molecular Immunology, 1985, vol. 22, No. 8, pp. 879–885.
Ng, James et al., Differentiation of Protein L–Containing and Albumin–Binding Peptostreptococcus magnus Isolates by DNA Amplification, Ribotyping, and Pulsed Field Gel Electrophoresis, 1996, Anaerobe, vol. 2, pp. 95–102.

(Continued)

*Primary Examiner*—Laurie Scheiner
(74) *Attorney, Agent, or Firm*—Kalow & Springut LLP

(57) ABSTRACT

The present invention is directed to an immunoglobulin light chain binding protein which comprises the amino acid sequence of SEQ ID NO:1 modified by an amino acid substitution at one or more of positions 39, 53 and 57 and/or by an amino acid insertion between positions 59 and 60 such that the dissociation constant (Kd) of the protein with respect to human immunoglobulin κ-chain is 400 nM or more at pH 8, or the amino acid sequence of a corresponding immunoglobulin light chain binding domain modified by an amino acid substitution at one or more of the positions equivalent to positions 39, 53 and 57 of SEQ ID NO:1 and/or by an amino acid insertion between positions equivalent to positions 59 and 60 of SEQ ID NO:1, such that the dissociation constant (Kd) of the protein with respect to human immunoglobulin κ-chain is 400 nM or more at pH 8, or the amino acid sequence of a fragment of (a) or (b) which contains at least one said substitution and/or insertion, such that the dissociation constant (Kd) of the protein with respect to human immunoglobulin κ-chain is 400 nM or more at pH 8.

5 Claims, 3 Drawing Sheets

OTHER PUBLICATIONS

Nilson, Bo H.K. et al., Protein L from Peptostreptococcus magnus Binds to the Kappa Light Chain Variable Domain, Feb. 5, 1992, J. Biol. Chem., vol. 267, No. 4, pp. 2234–2239.

Nilson, Bo H.K. et al., Purification of Antibodies Using Protein L–binding Framework Structures in the Light Chain Variable Domain, 1993, Journal of Immunological Methods, vol. 164, pp. 33–40.

Scalley, Michelle L. et al., Kinetics of Folding of the IgG Binding Domain of Peptostreptococcal Protein L, 1997, Biochemistry, vol. 36, pp. 3373–3382.

Sjobring, Ulf et al, Ig–binding Bacterial Proteins Also Bind Proteinase Inhibitors, Nov. 1, 1989, J. Biol. Chem., Vo. 143, No. 9, pp. 2948–2954.

Wikstrom, Mats et al., Three–dimesional Solution Structure of an Immunoglobulin Light Chain–binding Domain of Protein L: Comparison with the IgG–binding Domains of Protein G, 1994, Biochemistry, vol. 33, pp. 14011–14017.

Wikstrom, Mats et al., Backbone Dynamics of a Domain of Protein L Which Binds to Immunoglobulin Light Chains, 1996, Eur. J. Biochem., vol. 235, pp. 543–548.

Wikstrom, Mats et al., Proton Nuclear Magnetic Resonance Sequential Assignments and Secondary Structure of an Immunoglobulin Light Chain–binding Domain of Protein L, 1993, Biochemistry, vol. 32, pp. 3381–3386.

* cited by examiner

… (1) …

SEQUENCE LISTING

<160> NUMBER OF SEQ ID NOS: 32

<210> SEQ ID NO 1
<211> LENGTH: 249
<212> TYPE: DNA
<213> ORGANISM: Peptostreptococcus sp.
<220> FEATURE:
<221> NAME/KEY: CDS
<222> LOCATION: (1)...(246)

<400> SEQUENCE: 1

| atg aac att aaa ttt gct gga aaa gaa aca cca gaa aca cca gaa gaa | 48 |
| Met Asn Ile Lys Phe Ala Gly Lys Glu Thr Pro Glu Thr Pro Glu Glu | |
| 1               5                   10                  15     | |

| cca aaa gaa gaa gtt aca atc aaa gtt aac tta atc ttt gca gat gga | 96 |
| Pro Lys Glu Glu Val Thr Ile Lys Val Asn Leu Ile Phe Ala Asp Gly | |
|         20                  25                  30              | |

| aag ata caa aca gca gaa ttc aaa gga aca ttt gaa gaa gca aca gca | 144 |
| Lys Ile Gln Thr Ala Glu Phe Lys Gly Thr Phe Glu Glu Ala Thr Ala | |
|     35                  40                  45                  | |

| gaa gct tac aga tat gca gac tta tta gca aaa gta aat ggc gaa tat | 192 |
| Glu Ala Tyr Arg Tyr Ala Asp Leu Leu Ala Lys Val Asn Gly Glu Tyr | |
| 50                  55                  60                      | |

| aca gca gac tta gaa gat ggt gga aac cat atg aac att aaa ttt gct | 240 |
| Thr Ala Asp Leu Glu Asp Gly Gly Asn His Met Asn Ile Lys Phe Ala | |
| 65                  70                  75                  80  | |

| gga aaa taa | 249 |
| Gly Lys     |     |

<210> SEQ ID NO 2
<211> LENGTH: 82
<212> TYPE: PRT
<213> ORGANISM: Peptostreptococcus sp.

<400> SEQUENCE: 2

Met Asn Ile Lys Phe Ala Gly Lys Glu Thr Pro Glu Thr Pro Glu Glu
1               5                   10                  15

Pro Lys Glu Glu Val Thr Ile Lys Val Asn Leu Ile Phe Ala Asp Gly
            20                  25                  30

Lys Ile Gln Thr Ala Glu Phe Lys Gly Thr Phe Glu Glu Ala Thr Ala
        35                  40                  45

Glu Ala Tyr Arg Tyr Ala Asp Leu Leu Ala Lys Val Asn Gly Glu Tyr
    50                  55                  60

Thr Ala Asp Leu Glu Asp Gly Gly Asn His Met Asn Ile Lys Phe Ala
65                  70                  75                  80

Gly Lys

<210> SEQ ID NO 3
<211> LENGTH: 228
<212> TYPE: DNA
<213> ORGANISM: Peptostreptococcus sp.
<220> FEATURE:
<221> NAME/KEY: CDS
<222> LOCATION: (1)...(228)

<400> SEQUENCE: 3

```
aaa gaa gaa aca cca gaa aca cca gaa act gat tca gaa gaa gaa gta      48
Lys Glu Glu Thr Pro Glu Thr Pro Glu Thr Asp Ser Glu Glu Glu Val
 1               5                  10                  15 aca atc aaa gct aac cta atc ttt gca aat gga agc aca caa act gca      96
Thr Ile Lys Ala Asn Leu Ile Phe Ala Asn Gly Ser Thr Gln Thr Ala
             20                  25                  30 gaa ttc aaa gga aca ttt gaa aaa gca aca tca gaa gct tat gcg tat     144
Glu Phe Lys Gly Thr Phe Glu Lys Ala Thr Ser Glu Ala Tyr Ala Tyr
         35                  40                  45 gca gat act ttg aag aaa gac aat gga gaa tat act gta gat gtt gca     192
Ala Asp Thr Leu Lys Lys Asp Asn Gly Glu Tyr Thr Val Asp Val Ala
     50                  55                  60 gat aaa ggt tat act tta aat att aaa ttt gct gga                     228
Asp Lys Gly Tyr Thr Leu Asn Ile Lys Phe Ala Gly
 65                  70                  75
```

<210> SEQ ID NO 4
<211> LENGTH: 76
<212> TYPE: PRT
<213> ORGANISM: Peptostreptococcus sp.

<400> SEQUENCE: 4

```
Lys Glu Glu Thr Pro Glu Thr Pro Glu Thr Asp Ser Glu Glu Glu Val
 1               5                  10                  15

Thr Ile Lys Ala Asn Leu Ile Phe Ala Asn Gly Ser Thr Gln Thr Ala
             20                  25                  30

Glu Phe Lys Gly Thr Phe Glu Lys Ala Thr Ser Glu Ala Tyr Ala Tyr
         35                  40                  45

Ala Asp Thr Leu Lys Lys Asp Asn Gly Glu Tyr Thr Val Asp Val Ala
     50                  55                  60

Asp Lys Gly Tyr Thr Leu Asn Ile Lys Phe Ala Gly
 65                  70                  75
```

<210> SEQ ID NO 5
<211> LENGTH: 216
<212> TYPE: DNA
<213> ORGANISM: Peptostreptococcus sp.
<220> FEATURE:
<221> NAME/KEY: CDS
<222> LOCATION: (1)...(216)

<400> SEQUENCE: 5

```
aaa gaa aaa aca cca gaa gaa cca aaa gaa gaa gtt act att aaa gca      48
Lys Glu Lys Thr Pro Glu Glu Pro Lys Glu Glu Val Thr Ile Lys Ala
 1               5                  10                  15 aac tta atc tat gca gat gga aaa aca caa aca gca gaa ttc aaa gga      96
Asn Leu Ile Tyr Ala Asp Gly Lys Thr Gln Thr Ala Glu Phe Lys Gly
             20                  25                  30 aca ttt gaa gaa gca aca gca gaa gca tac aga tat gca gat gca tta     144
Thr Phe Glu Glu Ala Thr Ala Glu Ala Tyr Arg Tyr Ala Asp Ala Leu
         35                  40                  45 aag aag gac aat gga gaa tat aca gta gac gtt gca gat aaa ggt tat     192
Lys Lys Asp Asn Gly Glu Tyr Thr Val Asp Val Ala Asp Lys Gly Tyr
     50                  55                  60 act tta aat att aaa ttt gct gga                                     216
Thr Leu Asn Ile Lys Phe Ala Gly
 65                  70
```

<210> SEQ ID NO 6
<211> LENGTH: 72
<212> TYPE: PRT
<213> ORGANISM: Peptostreptococcus sp.

<400> SEQUENCE: 6

Lys Glu Lys Thr Pro Glu Glu Pro Lys Glu Glu Val Thr Ile Lys Ala
 1               5                  10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Ala Leu
        35                  40                  45

Lys Lys Asp Asn Gly Glu Tyr Thr Val Asp Val Ala Asp Lys Gly Tyr
    50                  55                  60

Thr Leu Asn Ile Lys Phe Ala Gly
65                  70

<210> SEQ ID NO 7
<211> LENGTH: 216
<212> TYPE: DNA
<213> ORGANISM: Peptostreptococcus sp.
<220> FEATURE:
<221> NAME/KEY: CDS
<222> LOCATION: (1)...(216)

<400> SEQUENCE: 7 aaa gaa aaa aca cca gaa gaa cca aaa gaa gaa gtt act att aaa gca     48
Lys Glu Lys Thr Pro Glu Glu Pro Lys Glu Glu Val Thr Ile Lys Ala
 1               5                  10                  15 aac tta atc tat gca gat gga aaa aca caa aca gca gaa ttc aaa gga     96
Asn Leu Ile Tyr Ala Asp Gly Lys Thr Gln Thr Ala Glu Phe Lys Gly
            20                  25                  30 aca ttt gaa gaa gca aca gca gaa gca tac aga tat gct gac tta tta    144
Thr Phe Glu Glu Ala Thr Ala Glu Ala Tyr Arg Tyr Ala Asp Leu Leu
        35                  40                  45 gca aaa gaa aat ggt aaa tat aca gta gac gtt gca gat aaa ggt tat    192
Ala Lys Glu Asn Gly Lys Tyr Thr Val Asp Val Ala Asp Lys Gly Tyr
    50                  55                  60 act tta aat att aaa ttt gct gga                                    216
Thr Leu Asn Ile Lys Phe Ala Gly
65                  70

<210> SEQ ID NO 8
<211> LENGTH: 72
<212> TYPE: PRT
<213> ORGANISM: Peptostreptococcus sp.

<400> SEQUENCE: 8

Lys Glu Lys Thr Pro Glu Glu Pro Lys Glu Glu Val Thr Ile Lys Ala
 1               5                  10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Leu Leu
        35                  40                  45

Ala Lys Glu Asn Gly Lys Tyr Thr Val Asp Val Ala Asp Lys Gly Tyr
    50                  55                  60

Thr Leu Asn Ile Lys Phe Ala Gly
65                  70

<210> SEQ ID NO 9
<211> LENGTH: 216
<212> TYPE: DNA
<213> ORGANISM: Peptostreptococcus sp.
<220> FEATURE:
<221> NAME/KEY: CDS

<222> LOCATION: (1)...(216)

<400> SEQUENCE: 9

| | | | | | | | | | | | | | | | | |
|---|---|---|---|---|---|---|---|---|---|---|---|---|---|---|---|---|
| aaa | gaa | aaa | aca | cca | gaa | gaa | cca | aaa | gaa | gaa | gtt | act | att | aaa | gca | 48 |
| Lys | Glu | Lys | Thr | Pro | Glu | Glu | Pro | Lys | Glu | Glu | Val | Thr | Ile | Lys | Ala | |
| 1 | | | | 5 | | | | | 10 | | | | | 15 | | |

| aac | tta | atc | tat | gca | gat | gga | aaa | act | caa | aca | gca | gag | ttc | aaa | gga | 96 |
|---|---|---|---|---|---|---|---|---|---|---|---|---|---|---|---|---|
| Asn | Leu | Ile | Tyr | Ala | Asp | Gly | Lys | Thr | Gln | Thr | Ala | Glu | Phe | Lys | Gly | |
| | | | 20 | | | | | 25 | | | | | 30 | | | |

| aca | ttt | gca | gaa | gca | aca | gca | gaa | gca | tac | aga | tac | gct | gac | tta | tta | 144 |
|---|---|---|---|---|---|---|---|---|---|---|---|---|---|---|---|---|
| Thr | Phe | Ala | Glu | Ala | Thr | Ala | Glu | Ala | Tyr | Arg | Tyr | Ala | Asp | Leu | Leu | |
| | | 35 | | | | | 40 | | | | | 45 | | | | |

| gca | aaa | gaa | aat | ggt | aaa | tat | aca | gca | gac | tta | gaa | gat | ggt | gga | tac | 192 |
|---|---|---|---|---|---|---|---|---|---|---|---|---|---|---|---|---|
| Ala | Lys | Glu | Asn | Gly | Lys | Tyr | Thr | Ala | Asp | Leu | Glu | Asp | Gly | Gly | Tyr | |
| | 50 | | | | | 55 | | | | | 60 | | | | | |

| act | att | aat | att | aga | ttt | gca | ggt | | | | | | | | | 216 |
|---|---|---|---|---|---|---|---|---|---|---|---|---|---|---|---|---|
| Thr | Ile | Asn | Ile | Arg | Phe | Ala | Gly | | | | | | | | | |
| 65 | | | | 70 | | | | | | | | | | | | |

<210> SEQ ID NO 10
<211> LENGTH: 72
<212> TYPE: PRT
<213> ORGANISM: Peptostreptococcus sp.

<400> SEQUENCE: 10

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Ala Glu Ala Thr Ala Glu Ala Tyr Arg Tyr Ala Asp Leu Leu
        35                  40                  45

Ala Lys Glu Asn Gly Lys Tyr Thr Ala Asp Leu Glu Asp Gly Gly Tyr
    50                  55                  60

Thr Ile Asn Ile Arg Phe Ala Gly
65                  70

<210> SEQ ID NO 11
<211> LENGTH: 213
<212> TYPE: DNA
<213> ORGANISM: Peptostreptococcus sp.
<220> FEATURE:
<221> NAME/KEY: CDS
<222> LOCATION: (1)...(213)

<400> SEQUENCE: 11

| aaa | gaa | aca | cca | gaa | cca | gaa | gaa | gaa | gtt | aca | atc | aaa | gct | aac | tta | 48 |
|---|---|---|---|---|---|---|---|---|---|---|---|---|---|---|---|---|
| Lys | Glu | Thr | Pro | Glu | Pro | Glu | Glu | Glu | Val | Thr | Ile | Lys | Ala | Asn | Leu | |
| 1 | | | | 5 | | | | | 10 | | | | | 15 | | |

| atc | ttt | gca | gat | gga | agc | aca | caa | aat | gca | gaa | ttc | aaa | gga | aca | ttc | 96 |
|---|---|---|---|---|---|---|---|---|---|---|---|---|---|---|---|---|
| Ile | Phe | Ala | Asp | Gly | Ser | Thr | Gln | Asn | Ala | Glu | Phe | Lys | Gly | Thr | Phe | |
| | | | 20 | | | | | 25 | | | | | 30 | | | |

| gca | aaa | gca | gta | tca | gat | gct | tac | gct | tac | gca | gat | gct | tta | aag | aaa | 144 |
|---|---|---|---|---|---|---|---|---|---|---|---|---|---|---|---|---|
| Ala | Lys | Ala | Val | Ser | Asp | Ala | Tyr | Ala | Tyr | Ala | Asp | Ala | Leu | Lys | Lys | |
| | | 35 | | | | | 40 | | | | | 45 | | | | |

| gac | aac | gga | gaa | tat | act | gta | gac | gtt | gca | gat | aaa | ggc | tta | act | tta | 192 |
|---|---|---|---|---|---|---|---|---|---|---|---|---|---|---|---|---|
| Asp | Asn | Gly | Glu | Tyr | Thr | Val | Asp | Val | Ala | Asp | Lys | Gly | Leu | Thr | Leu | |
| | 50 | | | | | 55 | | | | | 60 | | | | | |

| aat | att | aaa | ttc | gct | ggt | aaa | | | | | | | | | | 213 |
|---|---|---|---|---|---|---|---|---|---|---|---|---|---|---|---|---|
| Asn | Ile | Lys | Phe | Ala | Gly | Lys | | | | | | | | | | |
| 65 | | | | 70 | | | | | | | | | | | | |

<210> SEQ ID NO 12
<211> LENGTH: 71
<212> TYPE: PRT
<213> ORGANISM: Peptostreptococcus sp.

<400> SEQUENCE: 12

Lys Glu Thr Pro Glu Pro Glu Glu Val Thr Ile Lys Ala Asn Leu
1               5                   10                  15

Ile Phe Ala Asp Gly Ser Thr Gln Asn Ala Glu Phe Lys Gly Thr Phe
            20                  25                  30

Ala Lys Ala Val Ser Asp Ala Tyr Ala Tyr Ala Asp Ala Leu Lys Lys
        35                  40                  45

Asp Asn Gly Glu Tyr Thr Val Asp Val Ala Lys Gly Leu Thr Leu
    50                  55                  60

Asn Ile Lys Phe Ala Gly Lys
65                  70

<210> SEQ ID NO 13
<211> LENGTH: 213
<212> TYPE: DNA
<213> ORGANISM: Peptostreptococcus sp.
<220> FEATURE:
<221> NAME/KEY: CDS
<222> LOCATION: (1)...(213)

<400> SEQUENCE: 13 aaa gaa aaa cca gaa gaa cca aaa gaa gaa gtt aca atc aaa gtt aac      48
Lys Glu Lys Pro Glu Glu Pro Lys Glu Glu Val Thr Ile Lys Val Asn
1               5                   10                  15 tta atc ttt gca gat gga aag aca caa aca gca gaa ttc aaa gga aca      96
Leu Ile Phe Ala Asp Gly Lys Thr Gln Thr Ala Glu Phe Lys Gly Thr
            20                  25                  30 ttt gaa gaa gca aca gca aaa gct tat gct tat gca gac tta tta gca     144
Phe Glu Glu Ala Thr Ala Lys Ala Tyr Ala Tyr Ala Asp Leu Leu Ala
        35                  40                  45 aaa gaa aat ggc gaa tat aca gca gac tta gaa gat ggt gga aac aca     192
Lys Glu Asn Gly Glu Tyr Thr Ala Asp Leu Glu Asp Gly Gly Asn Thr
    50                  55                  60 atc aac att aaa ttt gct gga                                         213
Ile Asn Ile Lys Phe Ala Gly
65                  70

<210> SEQ ID NO 14
<211> LENGTH: 71
<212> TYPE: PRT
<213> ORGANISM: Peptostreptococcus sp.

<400> SEQUENCE: 14

Lys Glu Lys Pro Glu Glu Pro Lys Glu Glu Val Thr Ile Lys Val Asn
1               5                   10                  15

Leu Ile Phe Ala Asp Gly Lys Thr Gln Thr Ala Glu Phe Lys Gly Thr
            20                  25                  30

Phe Glu Glu Ala Thr Ala Lys Ala Tyr Ala Tyr Ala Asp Leu Leu Ala
        35                  40                  45

Lys Glu Asn Gly Glu Tyr Thr Ala Asp Leu Glu Asp Gly Gly Asn Thr
    50                  55                  60

Ile Asn Ile Lys Phe Ala Gly
65                  70

<210> SEQ ID NO 15
<211> LENGTH: 222

```
<212> TYPE: DNA
<213> ORGANISM: Peptostreptococcus sp.
<220> FEATURE:
<221> NAME/KEY: CDS
<222> LOCATION: (1)...(222)

<400> SEQUENCE: 15 aaa gaa aca cca gaa aca cca gaa gaa cca aaa gaa gaa gtt aca atc     48
Lys Glu Thr Pro Glu Thr Pro Glu Glu Pro Lys Glu Glu Val Thr Ile
 1               5                  10                  15 aaa gtt aac tta atc ttt gca gat gga aag ata caa aca gca gaa ttc     96
Lys Val Asn Leu Ile Phe Ala Asp Gly Lys Ile Gln Thr Ala Glu Phe
             20                  25                  30 aaa gga aca ttt gaa gaa gca aca gca aaa gct tat gct tat gca aac    144
Lys Gly Thr Phe Glu Glu Ala Thr Ala Lys Ala Tyr Ala Tyr Ala Asn
         35                  40                  45 tta tta gca aaa gaa aat ggc gaa tat aca gca gac tta gaa gat ggt    192
Leu Leu Ala Lys Glu Asn Gly Glu Tyr Thr Ala Asp Leu Glu Asp Gly
     50                  55                  60 gga aac aca atc aac att aaa ttt gct gga                            222
Gly Asn Thr Ile Asn Ile Lys Phe Ala Gly
 65                  70

<210> SEQ ID NO 16
<211> LENGTH: 74
<212> TYPE: PRT
<213> ORGANISM: Peptostreptococcus sp.

<400> SEQUENCE: 16

Lys Glu Thr Pro Glu Thr Pro Glu Glu Pro Lys Glu Glu Val Thr Ile
 1               5                  10                  15

Lys Val Asn Leu Ile Phe Ala Asp Gly Lys Ile Gln Thr Ala Glu Phe
             20                  25                  30

Lys Gly Thr Phe Glu Glu Ala Thr Ala Lys Ala Tyr Ala Tyr Ala Asn
         35                  40                  45

Leu Leu Ala Lys Glu Asn Gly Glu Tyr Thr Ala Asp Leu Glu Asp Gly
     50                  55                  60

Gly Asn Thr Ile Asn Ile Lys Phe Ala Gly
 65                  70

<210> SEQ ID NO 17
<211> LENGTH: 225
<212> TYPE: DNA
<213> ORGANISM: Peptostreptococcus sp.
<220> FEATURE:
<221> NAME/KEY: CDS
<222> LOCATION: (1)...(225)

<400> SEQUENCE: 17 aaa gaa aca cca gaa aca cca gaa gaa cca aaa gaa gaa gtt aca atc     48
Lys Glu Thr Pro Glu Thr Pro Glu Glu Pro Lys Glu Glu Val Thr Ile
 1               5                  10                  15 aaa gtt aac tta atc ttt gca gat gga aaa aca caa aca gca gaa ttc     96
Lys Val Asn Leu Ile Phe Ala Asp Gly Lys Thr Gln Thr Ala Glu Phe
             20                  25                  30 aaa gga aca ttt gaa gaa gca aca gca gaa gct tac aga tat gca gac    144
Lys Gly Thr Phe Glu Glu Ala Thr Ala Glu Ala Tyr Arg Tyr Ala Asp
         35                  40                  45 tta tta gca aaa gta aat ggt gaa tac aca gca gac tta gaa gat ggc    192
Leu Leu Ala Lys Val Asn Gly Glu Tyr Thr Ala Asp Leu Glu Asp Gly
     50                  55                  60 gga tac act atc aac atc aaa ttt gct gga aaa                        225
```

```
Gly Tyr Thr Ile Asn Ile Lys Phe Ala Gly Lys
 65                  70                  75

<210> SEQ ID NO 18
<211> LENGTH: 75
<212> TYPE: PRT
<213> ORGANISM: Peptostreptococcus sp.

<400> SEQUENCE: 18

Lys Glu Thr Pro Glu Thr Pro Glu Glu Pro Lys Glu Glu Val Thr Ile
 1               5                  10                  15

Lys Val Asn Leu Ile Phe Ala Asp Gly Lys Thr Gln Thr Ala Glu Phe
                20                  25                  30

Lys Gly Thr Phe Glu Glu Ala Thr Ala Glu Ala Tyr Arg Tyr Ala Asp
             35                  40                  45

Leu Leu Ala Lys Val Asn Gly Glu Tyr Thr Ala Asp Leu Glu Asp Gly
         50                  55                  60

Gly Tyr Thr Ile Asn Ile Lys Phe Ala Gly Lys
 65                  70                  75

<210> SEQ ID NO 19
<211> LENGTH: 249
<212> TYPE: DNA
<213> ORGANISM: Artificial Sequence
<220> FEATURE:
<223> OTHER INFORMATION: Ppl mutant
<221> NAME/KEY: CDS
<222> LOCATION: (1)...(246)

<400> SEQUENCE: 19 atg aac att aaa ttt gct gga aaa gaa aca cca gaa aca cca gaa gaa      48
Met Asn Ile Lys Phe Ala Gly Lys Glu Thr Pro Glu Thr Pro Glu Glu
 1               5                  10                  15 cca aaa gaa gaa gtt aca atc aaa gtt aac tta atc ttt gca gat gga      96
Pro Lys Glu Glu Val Thr Ile Lys Val Asn Leu Ile Phe Ala Asp Gly
                20                  25                  30 aag ata caa aca gca gaa cat aaa gga aca ttt gaa gaa gca aca gca     144
Lys Ile Gln Thr Ala Glu His Lys Gly Thr Phe Glu Glu Ala Thr Ala
             35                  40                  45 gaa gct tac aga tat gca gac tta tta gca aaa gta aat ggc gaa tat     192
Glu Ala Tyr Arg Tyr Ala Asp Leu Leu Ala Lys Val Asn Gly Glu Tyr
         50                  55                  60 aca gca gac tta gaa gat ggt gga aac cat atg aac att aaa ttt gct     240
Thr Ala Asp Leu Glu Asp Gly Gly Asn His Met Asn Ile Lys Phe Ala
 65                  70                  75                  80 gga aaa taa                                                         249
Gly Lys

<210> SEQ ID NO 20
<211> LENGTH: 249
<212> TYPE: DNA
<213> ORGANISM: Artificial Sequence
<220> FEATURE:
<223> OTHER INFORMATION: PpL mutant
<221> NAME/KEY: CDS
<222> LOCATION: (1)...(246)

<400> SEQUENCE: 20 atg aac att aaa ttt gct gga aaa gaa aca cca gaa aca cca gaa gaa      48
Met Asn Ile Lys Phe Ala Gly Lys Glu Thr Pro Glu Thr Pro Glu Glu
 1               5                  10                  15 cca aaa gaa gaa gtt aca atc aaa gtt aac tta atc ttt gca gat gga      96
Pro Lys Glu Glu Val Thr Ile Lys Val Asn Leu Ile Phe Ala Asp Gly
```

```
                20                  25                  30
aag ata caa aca gca gaa ttc aaa gga aca ttt gaa gaa gca aca gca      144
Lys Ile Gln Thr Ala Glu Phe Lys Gly Thr Phe Glu Glu Ala Thr Ala
            35                  40                  45 gaa gct tac aga aac gca gac tta tta gca aaa gta aat ggc gaa tat      192
Glu Ala Tyr Arg Asn Ala Asp Leu Leu Ala Lys Val Asn Gly Glu Tyr
 50                  55                  60 aca gca gac tta gaa gat ggt gga aac cat atg aac att aaa ttt gct      240
Thr Ala Asp Leu Glu Asp Gly Gly Asn His Met Asn Ile Lys Phe Ala
 65                  70                  75                  80 gga aaa taa                                                           249
Gly Lys <210> SEQ ID NO 21
<211> LENGTH: 249
<212> TYPE: DNA
<213> ORGANISM: Artificial Sequence
<220> FEATURE:
<223> OTHER INFORMATION: PpL mutant
<221> NAME/KEY: CDS
<222> LOCATION: (1)...(246)

<400> SEQUENCE: 21 atg aac att aaa ttt gct gga aaa gaa aca cca gaa aca cca gaa gaa      48
Met Asn Ile Lys Phe Ala Gly Lys Glu Thr Pro Glu Thr Pro Glu Glu
  1               5                  10                  15 cca aaa gaa gaa gtt aca atc aaa gtt aac tta atc ttt gca gat gga      96
Pro Lys Glu Glu Val Thr Ile Lys Val Asn Leu Ile Phe Ala Asp Gly
             20                  25                  30 aag ata caa aca gca gaa ttc aaa gga aca ttt gaa gaa gca aca gca      144
Lys Ile Gln Thr Ala Glu Phe Lys Gly Thr Phe Glu Glu Ala Thr Ala
            35                  40                  45 gaa gct tac aga tat gca gac tta gac gca aaa gta aat ggc gaa tgg      192
Glu Ala Tyr Arg Tyr Ala Asp Leu Asp Ala Lys Val Asn Gly Glu Trp
 50                  55                  60 aca gca gac tta gaa gat ggt gga aac cat atg aac att aaa ttt gct      240
Thr Ala Asp Leu Glu Asp Gly Gly Asn His Met Asn Ile Lys Phe Ala
 65                  70                  75                  80 gga aaa taa                                                           249
Gly Lys <210> SEQ ID NO 22
<211> LENGTH: 249
<212> TYPE: DNA
<213> ORGANISM: Artificial Sequence
<220> FEATURE:
<223> OTHER INFORMATION: PpL mutant
<221> NAME/KEY: CDS
<222> LOCATION: (1)...(246)

<400> SEQUENCE: 22 atg aac att aaa ttt gct gga aaa gaa aca cca gaa aca cca gaa gaa      48
Met Asn Ile Lys Phe Ala Gly Lys Glu Thr Pro Glu Thr Pro Glu Glu
  1               5                  10                  15 cca aaa gaa gaa gtt aca atc aaa gtt aac tta atc ttt gca gat gga      96
Pro Lys Glu Glu Val Thr Ile Lys Val Asn Leu Ile Phe Ala Asp Gly
             20                  25                  30 aag ata caa aca gca gaa ttc aaa gga aca ttt gaa gaa gca aca gca      144
Lys Ile Gln Thr Ala Glu Phe Lys Gly Thr Phe Glu Glu Ala Thr Ala
            35                  40                  45 gaa gct tac aga tat gca gac tta cat gca aaa gta aat ggc gaa tat      192
Glu Ala Tyr Arg Tyr Ala Asp Leu His Ala Lys Val Asn Gly Glu Tyr
 50                  55                  60
```

```
aca gca gac tta gaa gat ggt gga aac cat atg aac att aaa ttt gct    240
Thr Ala Asp Leu Glu Asp Gly Gly Asn His Met Asn Ile Lys Phe Ala
 65                  70                  75                  80 gga aaa taa                                                         249
Gly Lys
```

<210> SEQ ID NO 23
<211> LENGTH: 27
<212> TYPE: DNA
<213> ORGANISM: Artificial Sequence
<220> FEATURE:
<223> OTHER INFORMATION: Oligonucleotide used to generate mutations

<400> SEQUENCE: 23
taagtctgct gtccattcgc catttac                                       27

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide used to generate mutations

<400> SEQUENCE: 24
tgttccttta tgttctgctg t                                             21

<210> SEQ ID NO 25
<211> LENGTH: 27
<212> TYPE: DNA
<213> ORGANISM: Artificial Sequence
<220> FEATURE:
<223> OTHER INFORMATION: Oligonucleotide used to generate mutations

<400> SEQUENCE: 25
taataagtct gcgtttctgt aagcttc                                       27

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide used to generate mutations

<400> SEQUENCE: 26
taagtctgca tgtctgtaag c                                             21

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide used to generate mutations

<400> SEQUENCE: 27
atttactttt gcgtctaagt ctgcata                                       27

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide used to generate mutations

<400> SEQUENCE: 28
tacttttgca tgtaagtctg c                                             21

```
<210> SEQ ID NO 29
<211> LENGTH: 30
<212> TYPE: DNA
<213> ORGANISM: Artificial Sequence
<220> FEATURE:
<223> OTHER INFORMATION: Oligonucleotide used to generate mutations

<400> SEQUENCE: 29
ttcgccattt acaccttttg ctaataagtc                                    30

<210> SEQ ID NO 30
<211> LENGTH: 21
<212> TYPE: DNA
<213> ORGANISM: Artificial Sequence
<220> FEATURE:
<223> OTHER INFORMATION: Oligonucleotide used to generate mutations

<400> SEQUENCE: 30
aaatttaatg tccatatggt t                                             21

<210> SEQ ID NO 31
<211> LENGTH: 33
<212> TYPE: DNA
<213> ORGANISM: Artificial Sequence
<220> FEATURE:
<223> OTHER INFORMATION: primer for the A2N mutation

<400> SEQUENCE: 31
caggaaacag accatgaaca ttaaatttgc tgg                                33

<210> SEQ ID NO 32
<211> LENGTH: 35
<212> TYPE: DNA
<213> ORGANISM: Artificial Sequence
<220> FEATURE:
<223> OTHER INFORMATION: primer for the F39W mutation

<400> SEQUENCE: 32
caaacagcag aatggaaagg aacatttgaa gaagc                              35
```

IMMUNOGLOBULIN BINDING PROTEIN

CROSS-REFERENCE TO RELATED APPLICATIONS

This application is a continuation under 35 U.S.C. §111(a) of International Patent Application No. PCT/GB99/03048 filed Sep. 14, 1999, now pending, which application claims the benefit of United Kingdom Patent Application No. 98 19998.7 filed Sep. 14, 1998 and United Kingdom Patent Application No. 9909578:8 filed Apr. 26, 1999; which applications are incorporated by reference herein in their entirety.

The invention relates to proteins capable of binding immunoglobulin light chains and in particular to modified light chain binding domains of protein L.

Protein L is an immunoglobulin light chain binding protein expressed on the surface of approximately 10% of *Peptostreptococcus* strains. Protein L is a multi-domain protein and has repeat domains showing a substantial degree of homology with each other, capable of binding to the light chains of immunoglobulin. Protein L has been isolated from two strains of *Peptostreptococcus* and has been cloned and studied in detail Kastern et al, J Biol Chem, 1992, 267, 18. 12820–12825 describes the cloning and expression of protein L from *Peptostreptococcus* strain 312 Murphy et al, Molecular Microbiology, 1994, 12(6), 911–920 describe cloning and expression of protein L from Peptostreptococcus strain 3316.

Strain 312 protein L has five immunoglobulin binding domains B1, B2, B3, B4 and B5. Strain 3316 protein L has four immunoglobulin binding domains C1, C2, C3 and C4. Each domain has the capacity to bind the light chains and in particular the κ-light chains of human IgG, IgA, IgD, IgE and IgM. Protein L also binds to rabbit, porcine, mouse and rat immunoglobulins. Because protein L interacts with the light chains of immunoglobulins, it has the capacity to bind to Fab and Fv fragments.

The broad spectrum of binding exhibited by protein L makes it a key candidate for use in isolation of immunoglobulins or immunoglobulin fragments from a sample. Protein L can be used to purify the immunoglobulins or immunoglobulin fragments for their subsequent use. In some circumstances it may be desirable to remove immunoglobulins or immunoglobulin fragments from a sample so that they do not interfere with the subsequent use of the sample.

A protein L construct comprising four binding domains from strain 312 has previously been used to isolate and purify antibodies. This construct has proved highly effective in removing antibodies from a sample. Each of the domains has the capacity to bind immunoglobulin. However, it has been found necessary in some instances to use harsh conditions, such as glycine-HCl buffer at pH 2.0, to elute antibody bound to this construct.

PpL is a construct based on the C3 domain of protein L from strain 3316 with 7 additional amino acids at the N-terminal and six internal substitutions from the C4 domain. Its preparation and expression are described in Bottomley et al, Bioseparation. 1995, 5, 359–367. The amino acid sequence of the PpL construct is shown in SEQ ID NO: 1, and also in SEQ ID NO:2. The PpL construct required 0.5M acetic acid for elution of κ-chain.

Protein L typically has a binding affinity for antibodies of about 2 to $3 \times 10^9$ $M^{-1}$. Although therefore protein L is useful for isolation of a broad spectrum of antibodies and fragments thereof, it would be desirable if milder conditions could be used to elute antibodies from a protein L-solid support. We have now found that this goal can be achieved by using specific mutated protein L derivatives. The binding affinity of these derivatives for the light chain of immunoglobulin is reduced compared to the corresponding unmutated polypeptide.

Accordingly, the present invention provides an immunoglobulin light chain binding protein which comprises:

(a) the amino acid sequence of SEQ ID NO: 1 modified by an amino acid substitution at one or more of positions 39, 53 and 57 and/or by an amino acid insertion between positions 59 and 60 such that the dissociation constant (Kd) of the protein with respect to human immunoglobulin κ-chain is 400 nM or more at pH8, or (b) the amino acid sequence of a corresponding immunoglobulin light chain binding domain modified by an amino acid substitution at one or more of the positions equivalent to positions 39, 53 and 57 of SEQ ID NO: 1 and/or by an amino acid insertion between positions equivalent to positions 59 and 60 of SEQ ID NO: 1, such that the dissociation constant (Kd) of the protein with respect to human immunoglobulin κ-chain is 400 nM or more at pH8, or (c) the amino acid sequence of a fragment of (a) or (b) which contains at least one said substitution and/or insertion such that the dissociation constant (Kd) of the protein with respect to human immunoglobulin κ-chain is 400 nM or more at pH 8.

Figure 1:
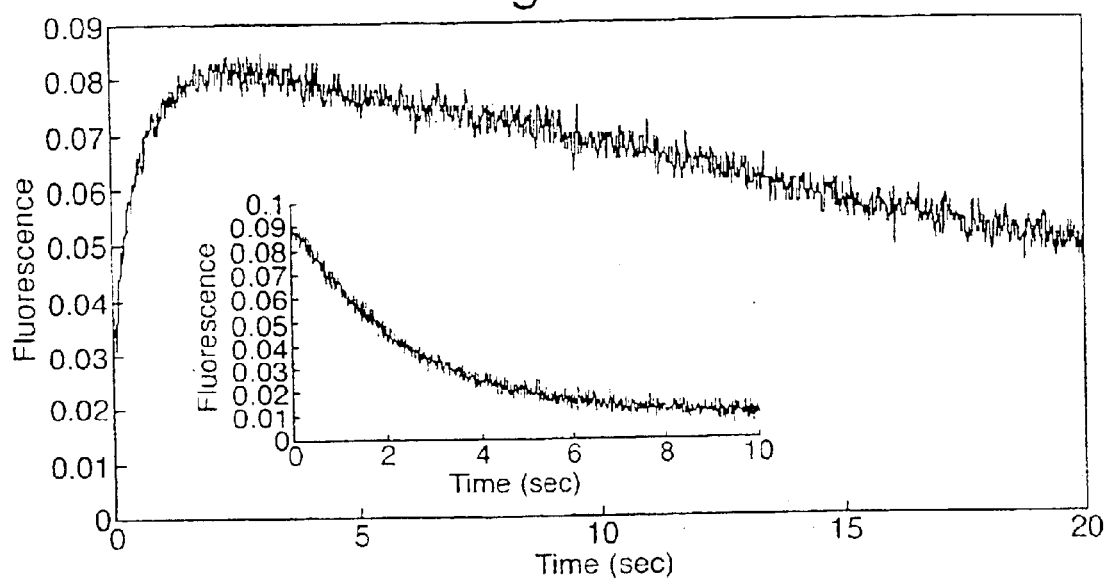
FIG. 1. Stopped flow fluorescence profile of 40 μM L57HY64W. PpL mixed in a 1:1 ratio with 4 μM Kappa, followed over a 20 second time course. Inset spectra of L57HY64W Kappa complex mixed with a 1:1 ratio with 40 μM Wt PpL, showing the dissociation of the complex followed over a 10 second time course.

The proteins of the invention all incorporate a domain which has the ability to bind to the light chains of immunoglobulins and in particular the κ-light chains of immunoglobulins. In general, the protein can bind to all types of human immunoglobulin, i.e. human IgG, IgA, IgD, IgE and IgM. The proteins preferably have the ability to bind to rabbit, porcine, mice and/or rat immunoglobulins. The protein preferably also binds to Fab and Fv fragments.

The proteins of the present invention thus consist essentially of amino acid sequence (a), (b) or (c). Multiples of a sequence may be present, for example two to five repeats of a sequence. A combination of sequences may be present. Thus, two or all three of sequences (a), (b) and (c) may be present.

Amino acid sequence (a) is derived from the amino acid sequence of SEQ ID NOS: 1 and 2 of the PpL construct. Amino acid sequence (b) is derived from the amino acid sequence of an immunoglobulin light chain binding domain that corresponds to such a domain of the PpL construct. Preferably, amino acid sequence (b) is derived from an immunoglobulin light chain binding domain of protein L.

Preferred examples of corresponding immunoglobulin light chain binding domains are the domains C1, C2, C3, C4, B1, B2, B3, B4 and B5 referred to above. The amino acid sequences of these domains are set out as follows:
strain 312 protein L domain B1: SEQ ID NOS: 3 and 4
strain 312 protein L domain B2: SEQ ID NOS: 5 and 6
strain 312 protein L domain B3: SEQ ID NOS: 7 and 8
strain 312 protein L domain B4: SEQ ID NOS: 9 and 10
strain 3316 protein L domain C1: SEQ ID NOS: 11 and 12
strain 3316 protein L domain C2: SEQ ID NOS: 13 and 14
strain 3316 protein L domain C3: SEQ ID NOS: 15 and 16
strain 3316 protein L domain C4: SEQ ID NOS: 17 and 18.

Other strains of *Peptostreptococcus* may also express protein L. Such protein L variants can be isolated following the cloning methods described in Kastern et al and Murphy et al, if necessary using nucleotide sequences disclosed therein as probes. Discrete domains which bind immunoglobulin light chains, typically κ-chain, can then be identified.

The amino acid sequences of the PpL construct and a corresponding immunoglobulin light chain binding domain can be lined up to establish which amino acids of that domain are equivalent to PpL amino acids 39, 53, 57, 59 and 60. For example, the nucleotide and amino acid sequences of PpL are lined up against the amino acid sequences of protein L domains C1 to C4 in Bottomley et al, 1995. The amino acid sequence of the C1 to C4 domains is lined up against that of the B1 to B5 domains in Murphy et al, 1994. The amino acid sequences of the C1 to C4 domains are also lined up against each other in Murphy et al, 1994, using the PILEUP program as implemented in the GCG package (Devereux et al, Nucl. Acids Res 12, 387–395, 1984)

The amino acid residues equivalent to PpL residues 39, 53 57, 59 and 60 can thus be readily deduced. As an example, the tyrosine residues which are equivalent to tyrosine 53 of PpL are Tyr 42 of C1, Tyr 43 of C2, Tyr 46 of C3, Tyr 46 of C4, Tyr 44 of B2, Tyr 44 of B3, Tyr 44 of B4 Tyr 46 of B5 and Tyr 48 of B1.

Amino acid sequence (a) incorporates an amino acid substitution at one or more of positions 39, 53 and 57 and/or an amino acid substitution between positions 59 and 60. Amino acid sequence (b) incorporates at least one corresponding amino acid substitution and/or insertion. This substitution is designed to reduce the affinity of the binding domain for immunoglobulin light chain, in particular κ-chain.

The binding affinity for κ-chain of immunoglobulin, particularly human κ-chain of the resulting modified protein is less than that of the unmodified protein. Conversely, the dissociation constant (Kd) is higher. The binding affinity is the inverse of the dissociation constant. Preferably the substitution/insertion according to the invention increases the Kd, i e. reduces the binding affinity, with respect to human κ-chain by about 10 to 30 fold. The Kd may therefore be 1 μM or more, 2 μM or more or 3 μM or more. The Kd may be increased up to 6 μM, to 10 μM or to 20 μM. Kd is determined at pH 8, using whole immunoglobulin IgG as described for example in the examples. Equally well, κ chains alone could be used to calculate binding affinity or dissociation constants. A different Kd will be obtained for κ-chain vs whole immunoglobulin. Peptides of the invention may show a reduction in affinity for κ-chains alone, whole immunoglobulin or both.

Suitable amino acid substitutions at one or more of PpL positions 39, 53 and 57, or at equivalent positions of a corresponding κ-chain binding domain, may be determined by routine experimentation. In general the or each substitution will be a non-conservative substitution. However, that does not mean that all characteristics of the original amino acid need to be altered by the substitution. Considerations which may be borne in mind when selecting an appropriate substitution are as follows:

PpL position 39/corresponding position of other κ-chain binding domain

The replacement of the phenylalanine residue having an aromatic side chain by a basic amino acid, histidinie, substantially increased Kd whereas replacement of the phenylalanine by tryptophan hardly increased Kd at all. Tryptophan also has an aromatic side chain. An amino acid with a polar side chain, for example a basic amino acid such as histidine, may therefore be considered in place of phenylalanine.

PpL position 53/Corresponding Position of Other κ-chain Binding Domain

The aromatic amino acid tyrosine occurs at PpL position 53. Tyrosine has a hydroxy group in its side chain. Replacement of the tyrosine residue by a basic amino acid, histidine, or by an aromatic amino acid lacking a side-chain having hydroxy group, phenylalanine, substantially increased Kd.

The aromatic nature of the side chain remains unchanged when tyrosine is substituted by phenylalanine. However, this change does increase the hydrophobic nature of the residue and has the effect of removing a hydroxyl residue. This affects the environment of this amino acid residue and thus has an effect on the binding of light chain of immunoglobulin.

An amino acid with a side chain which lacks a hydroxy group, for example a basic amino acid such as histidine or a non-polar aliphatic or aromatic amino acid such as phenylalanine or trytophan, may therefore be considered in place of tyrosine.

PpL position 57/Corresponding Position of Other κ-chain Binding Domain

The non-polar hydrophobic aliphatic amino acid leucine occurs at PpL position 57. Replacement of leucine with the polar charged amino acids aspartic acid and histidine substantially increased Kd. A polar amino acid which is aromatic or aliphatic such as aspartic acid or histidine may therefore be considered in place of leucine.

As far as the insertion of an amino acid residue between PpL positions 59 and 60 or between corresponding positions of another κ-chain binding domain is concerned, a non-polar amino acid residue may be inserted. The inserted residue may be an aliphatic residue such as glycine or alanine.

With reference to PpL, preferred substitutions are histidine at position 39, phenylalanine at position 53 and aspartic acid or histidine at position 57. A preferred insertion between positions 59 and 60 is glycine. Alteration of a residue to histidine has the added advantage that this residue may be uncharged or positively charged depending on the pH of the solution. Thus, the environment surrounding this amino acid may be changed through a change in the pH which facilitates elution of bound light chains from the protein.

A competitive enzyme linked immunosorbant assay (ELISA) can be used to determine the Kd with respect to human immunoglobulin κ-chain of a protein of the invention. It is thus a straightforward matter to assess whether an amino acid substitution or insertion has the desired effect of reducing binding affinity and thus shows an increase in the dissociation constant Kd when compared to wild type. Kd is determined at pH 8. The temperature is typically room temperature (15 to 20° C.). A 20 mM potassium phosphate buffer is typically used.

As is well known to those skilled in the art, the dissociation constant Kd will vary depending on the particular conditions. For example, changes in the salt concentration or the method by which a protein has been purified can lead to variations in the dissociation constant. The figures which are given herein for the dissociation constant should be considered as approximate figures. Variations of up to 50 or 60% in the dissociation constant can be achieved simply through a change in the salt concentration.

While it is suggested that the Kd be determined by competitive ELISA, other methods are well known to those skilled in the art for determining the value of Kd. For example, the dissociation constant can be determined by fluorescence spectroscopy, stopped flow fluorescence or isothermal titration calorimetry, circular dichroism spectroscopy, NMR or gel filtration. Examples of determination of the dissociation constant using these methods are set out in more detail below. In general, the mutation will give rise to a 30 fold decrease in the affinity of the polypeptide for κ-chain or immunoglobulin although the decrease in an affinity may be anywhere between a 10 fold decrease up to a 100 fold decrease in affinity.

The examples below describe binding between the constructs and immunoglobulins containing a chain which is probably characterised as κ1. Those skilled in the art will appreciate that different κ chains such as κ1, 3 or 4 man demonstrate different dissociation constants.

As noted above, an immunoglobulin light chain binding domain corresponding to SEQ ID NO: 1 may be the domain B1, B2, B3, B4 or B5 of Kastern et al, 1992, or the domain C1, C2, C3 or C4 of Murphy et al, 1994. A corresponding domain may however be a variant of one of domains B1 to B5 or C1 to C4, for example a naturally occurring alielic variant or a variant which is substantially homologous to one of these domains.

In this context substantial homology is regarded as a sequence which has at least 60% or at least 70%, e.g. at least 80% or at least 90%, amino acid homology (identity) with the sequence of one of domains B1 to B5 or C1 to C4. The homology may be up to 95% or up to 99%. Such a variant therefore may contain one or more, e.g. from 2, 3 or 5, up to 10 or 15 substitutions, deletions or insertions, including conserved substitutions. Homology may be determined using the FastA program from the GCG package.

Conserved substitutions may be made according to the following Table. Amino acids in the same block in the second column and preferably in the same line in the third column may be substituted for each other

TABLE 1

| Conserved substitutions | | |
|---|---|---|
| ALIPHATIC | Non-polar | G A |
| | | I L V |
| | Polar-uncharged | C S T M |
| | | N Q |
| | Polar-charged | D E |
| | | K R H |
| AROMATIC | | F W Y |
| OTHER | | N Q D E P |

Preferred substitutions can in particular be identified by comparison with the naturally occurring immunoglobulin binding domains and establishing substitutions found among these natural variants.

Amino acid sequence (c) is a fragment of sequence (a) or (b). Suitable fragments may be from 10 or from 20, for example from 40, up to 50, 55 or 60 amino acids in length.

The protein of the present invention may be provided as a multi-domain construct comprising at least one domain modified in accordance with the invention together with one or more other protein L light chain binding domains. For example, the protein may comprise 2, 3 or more, for example up to 5, domains. Multiples of the same modified domains, mixtures of different modified domains or mixtures of modified and unmodified domains may be present. The domains can be selected to achieve a desired affinity for light chains of immunoglobulin. By combining domains having different modifications, a library of fusion proteins can be built up to cover a range of desired binding affinities. Preferably the multi-domain protein will comprise no more than four domains and most preferably comprises 2 or 3 domains.

An amino acid sequence (a), (b) or (c) may be used to produce a hybrid protein with one or more other domain, such as a Fc binding domain. For such a hybrid protein, a domain which binds to immunoglobulin heavy chains may be chosen from the C1-, C2- and C3-domains in protein G, the A-, B- and C1-domains from protein H; the A-, B1-, B2- and S-domains in protein M1 and the E-, D-, A-, B-and C-domains in protein A. Such hybrid proteins can have a particularly broad spectrum of immunoglobulin binding.

Other domains may be incorporated to take advantage of the specific binding properties of such other domains combined with light chain binding domains of the present invention. A particularly preferred hybrid protein comprises at least one light chain binding domain of protein L modified in accordance with the present application together with an Fc binding domain of protein A. This hybrid combines a very broad spectrum of serum immunoglobulin binding with the ability to interact with the majority of human scFv and Fab antibodies.

When producing hybrid proteins having binding domains for different entities, it may be desirable to select the portions of the protein such that the Kd for each entity is about the same.

In fusion or hybrid proteins, the domains may be joined by a linker polypeptide. Any linker may be used as long as it does not interfere significantly with the correct conformation of the domains or with the immunoglobulin binding activity of the protein.

A protein of the invention may be in a substantially isolated form. It will be understood that the protein may be mixed with carriers or diluents which will not interfere with the intended purpose of the protein and still be regarded as substantially isolated. A protein of the invention may also be in a substantially purified form, in which case it will generally comprise the protein in a preparation in which more than 90%, e.g. 95%, 98% or 99%, by weight of protein in the preparation is a protein of the invention.

Proteins of the invention are typically provided on a solid support for immunoaffinity chromatography. They may be modified by addition of one or more amino acid residues to facilitate binding to the solid support. For example a cysteine residue may be added for attachment to a further cysteine or thiol-reacting group on a solid matrix, histidine added for attachment to zinc on a support or for binding to an agarose gel or mussel-derived adhesive protein for attachment to surfaces such as cellulose. Preferably these modifications will not effect the binding of the immunoglobulin light chains. If two or more light chain binding domains are incorporated into the protein, one of the domains may be used to provide sites for binding to supports etc.

A protein of the invention may be labeled with a revealing label. The revealing label may be any suitable label which allows the protein to be detected. Suitable labels include radioisotopes, e.g. $^{125}$I, enzymes, antibodies, polynucleotides and linkers such as biotin. Labeled proteins of the invention may be used in diagnostic procedures such as immunoassays in order to determine the amount of immunoglobulin or of a polypeptide of the invention in a sample.

A polypeptide or labeled polypeptide of the invention or fragment thereof may also be fixed to a solid phase, for example the surface of an immunoassay well or dipstick. Such labeled and/or immobilised polypeptides man be packaged into kits in a suitable container along with suitable reagents, controls, instructions and the like. Such polypeptides and kits may be used in methods of purification of antibodies.

Thus the proteins can be handled in a freeze-dried state or in a PBS-solution (phosphate-buffered physiological salt solution) pH 7.2 with 0.02% NaN$_3$. It can also be used connected to a solid phase, such as carbohydrate-based phases, for instance CNBr-activated sepharose, agarose, plastic surfaces, polyacrylamide, nylon, paper, magnetic spheres, filter, films. The proteins may be marked with biotin, alkaline phosphatase, radioactive isotopes, fluorescein and other fluorescent substances, gold particles, ferritin, and substances which enable luminescence to be measured.

Polypeptides and proteins of the invention may be chemically modified, e.g. post-translationally modified. For example, they may be glycosylated or comprise modified amino acid residues. Such modified polypeptides and proteins fall within the scope of the terms "polypeptide" and "protein" of the invention.

Polynucleotides of the invention comprise nucleic acid sequences encoding the polypeptides of the invention. Polynucleotides of the invention may comprise DNA or RNA. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art.

Preferred polynucleotides of the invention also include polynucleotide encoding any modified domains of the invention as described above. It will be understood by a skilled person that numerous different polynucleotides can encode the same polypeptide as a result of the degeneracy of the genetic code.

Polynucleotides encoding the desired substituted domains maybe prepared by site-directed mutagenesis on polynucleotides encoding the unmodified domains, for example, using appropriate fragments encoding the naturally occurring protein L domains.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and cultivating the host cell under conditions which bring about replication of the erector. The vector may be recovered from the host cell. Suitable host cells are described below in connection with expression vectors. Bacterial cells, especially *E. coli* are preferred.

The vectors may be for example, plasmid virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gTene for a mammalian vector.

Preferably, a polynucleotide of the invention in a vector is operably linked to regulatory sequences capable of effecting the expression of the coding sequence by the host cell, i.e. the vector is an expression vector. Such expression vectors can be used to express the polypeptides of the invention.

The term "operably linked" refers to a juxtaposition wherein the components described are in a relationship permitting them to function in their intended manner. A regulatory sequence "operably linked" to a coding sequence is positioned in such a way that expression of the coding sequence is achieved under conditions compatible with the regulatory sequences.

Such vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides.

Expression vectors of the invention may be introduced into host cells using conventional techniques including calcium phosphate precipitation, DEAE-dextran transfection, or electroporation.

Suitable cells include cells in which the above-mentioned vectors may be expressed. These include microbial cells such as bacteria such as *E. coli* plant cells, mammalian cells such as CHO cells. COS7 cells or Hela cells, insect cells or yeast such as *Saccharomyces*, Transgenic animals, birds or plants capable of expressing a protein of the invention may be used.

Cell culture can take place under standard conditions. Commercially available cultural media for cell culture are widely available and can be used in accordance with manufacturers' instructions.

The invention provides a process for the production of a protein of the invention by recombinant means. The process typically comprises: cultivating a transformed cell as defined above under conditions that allow expression of the protein and recovering the said protein.

Hybrid proteins of the invention will typically be prepared by joining together the polynucleotides encoding the monomers in the correct reading frame, then expressing the composite polynucleotide coding sequence under the control of regulatory sequences as defined herein. These composite polynucleotide coding sequences are a further aspect of the invention, as are vectors comprising them, methods of producing them by recombinant means, and cells comprising such vectors. It will be understood that proteins of the invention may be such fusion proteins.

The proteins of the present invention may be used in the separation, isolation, or purification of immunoglobulins or κ-chain containing immunoglobulin fragments. They may be used in the detection of such immunoglobulins or immunoglobulin fragments. The immunoglobulins or immunoglobulin fragments are typically human.

For these purposes, the proteins may usefully be bound to a solid support such as an agarose gel. The support is typically provided in the form of a column. A sample may then be applied to the support so that immunoglobulins or immunoglobulin fragments may be bound to the support. The immunoglobulins may then be eluted from the support. The conditions required for this elution step are less harsh than those previously used when Protein L was employed, thereby reducing the potential disruption of immunoglobulin function.

Binding to the support, or more specifically to a protein of the invention on the support, generally occurs most strongly at about pH 8. Elution may therefore be achieved by increasing the pH to from 8.5 to 10 such as to from 9 to 10, by decreasing the pH to from 3 to 4 or by increasing the salt concentration to 0.7 to 0.8 M.

The following Examples illustrates the invention. The one letter code for amino acids is used in the Examples. The substitution of tryptophan for tyrosine for example at position 64 allows fluorescence studies to be carried out. This substitution does not significantly effect the binding to immunoglobulin. Constructs incorporating this substitution alone do not form part of the invention.

Example 1

Mutagenesis

The cloning, expression and purification, of PpL is described in Bottomley et al, *Bioseparation*, 1995, 5, 359–367. PpL mutants were produced by site-directed mutagenesis and subsequent expression of the mutated PpL gene. Site-directed mutagenesis was carried out using the Kunkel method (Kunkel et al, Methods in Enzymol 1987, 154, 367–382). The oligonucleotides used to generate mutations at specific positions were:

Y64W (substitution of the tyrosine residue at amino acid position 64 by tryptophan):

```
5' TAAGTCTGCTGTCCATTCGCCATTTAC-3';     (SEQ ID NO:23)

F39H: 5'-TGTTCCTTTATGTTCTGCTGT-3';     (SEQ ID NO:24)

(SEQ ID NO:25)
Y53F: 5'-TAATAAGTCTGCGTTTCTGTAAGCTTC-3';

YS3H: 5'-TAAGTCTGCATGTCTGTAAGC-3';    (SEQ ID NO:26)

(SEQ ID NO:27)
L57D: 5'-ATTTACTTTTGCGTCTAAGTCTGCATA-3';

L57H: 5'-TACTTTTGCATGTAAGTCTGC-3';    (SEQ ID NO:28)

59G60 (G inserted between positions 59 and 60):

5'-TTCGCCATTTACACCTTTTGCTAATAAGTC-3'  (SEQ ID NO:29)

N76D: 5'-AAATTTAATGTCCATATCCTT-3'.    (SEQ ID NO:30)
```

The following mutations were generated likewise F39W, Q35E, Q35C, E38Q, Y53W, L57K, K59G and K40I. The mutations were confirmed by DNA sequencing and the mutant proteins were prepared as described in Bottomley et al, 1995.

More specifically, *E. coli* JM103 cells were made competent and transformed with a mutated PpL gene. A small 10 ml culture of LB broth supplemented with 50 µg/ml ampicillin was inoculated with the JM103 cells. The culture was grown at 37° C. overnight in an orbital shaker. This culture was then used to inoculate 41 of LB broth supplemented with 50 µg/ml ampicillin. The culture was grown at 37° C. until $A_{600}$) 0.7–0.9 was attained, upon which 0.6 mM isopropyl-β-D-thiogalactopyranoside (IPTG) was added. The cells were harvested after overnight growth by centrifugation for 20 min at 5500 rpm in a Sorval 3RB and stored frozen at −20° C. until needed.

Each clone was expressed in *E. coli* JM103 cells at a level of approximately 50 mg/liter of culture. To extract the desired PpL mutant protein, the cell paste was thawed and washed with buffer A (20 mM phosphate buffer, pH 8.5, 1 mM EDTA, 0.1 mM EGTA and 0.1 mM PMSF). The suspension was then sonicated (5×30 s bursts, MSE soniprep 150) and placed at 80° C. for 1 h and then centrifuged down at 12,000 rpm for 20 min. The resulting supernatant was then diluted 1:1 with buffer A and applied to a Q-Sepharose column (2 cm×15 cm) that had been equilibrated with buffer A. The column was washed with buffer A and the protein eluted with a linear gradient of 0–400 mM NaCl in 20 mM phosphate buffer, pH 8.5 at a flow rate of 1.25 ml/min. The eluate was monitored at 280 nm and collected into 6 ml fractions. The fractions containing the PpL mutant protein were pooled, dialyzed extensively against water and lyophilised.

The following PpL mutants were thus obtained:
invention: Y53F PpL, Y53F Y64W PpL, F39H PpL (SEQ ID NO 19), F39H Y64W PpL, Y53H F39W PpL, Y53F PpL (SEQ ID NO: 20), Y53F Y64W PpL, Y53W PpL, L57D Y64W PpL (SEQ ID NO 21), L57H
   PpL (SEQ ID NO 22), L57H Y64W PpL, 59G60 PpL and N76D PpL.
others Y64W PpL, F39W PpL, Q35E Y64N, PpL, Q35E F39W PpL and 59G60 PpL.

Interaction Between Y64W PpL and Human κ-chain

PpL contains no native tryptophan residues. Therefore a tryptophan residue was inserted in place of a tyrosine residue at amino acid position 64. This substitution allowed fluorescence studies to be used to look at the binding of κ-light chains to protein L. Tryptophan fluorescence emission is sensitive to the immediate environment of the tryptophan residue, and has been used to monitor binding interactions of protein L.

When $Y_{64}W$ PpL was in complex with κ-chain, there was a 9% quench in fluorescence emission relative to the addition of the spectra of the individual proteins. The wavelength maximum of Y64W PpL is 336 nm, which shifted to 338 nm in the complex, suggesting the typtophan residue had not entered a significantly different environment in the complex.

The dissociation constant Kd for the interaction between Y64W PpL and IgG was determined by competitive ELISA. The Kd for Y64W PpL was found to be 129±17 nM which compared favourably to the Kd previously determined for PpL (112±20 nM). This suggested that there was little difference in the binding affinity of the two proteins.

Fluorescence Studies of Y53F PpL

The quantum yield of fluorescence of Y53F PpL at 302 nm was 34% lower than PpL, which corresponded to the removal of one third of the residues contributing to the fluorescence. However, there was no change in the fluorescence emission of the Y53F PpL κ-chain complex compared to the sum of the fluorescence emission of the individual proteins at 302 nm. This suggested that the quench in fluorescence observed with the formation of the PpL κ-chain complex was due to a decrease in emission from the tyrosine residue at position 53.

The Y53F mutation was also made on the Y64W PpL protein. There was a 10% increase in fluorescence signal of the Y53F Y64W PpL κ-chain complex relative to the sum of the fluorescence from the individual proteins. This increase thus contrasted with the 9% quench in fluorescence observed on the formation of the Y64W PpL κ-chain complex.

Enzyme Linked Immunosorbant Assay

A competitive ELISA was used to establish the $Kd_{app}$ for each PpL mutant with human IgG. Wells of a microtitre plate were coated with 0.008 mg PpL using sodium carbonate buffer, pH 9.5 at 37° C. for 2 hours. Following three washes with PBST (phosphate buffer saline-0.1% v/v Tween 20), 100 μl 0.08 to 2.5 mg/ml of each PpL mutant was added to row 2 and serially diluted across the plate, whilst row 12 was left with no competing protein as control for maximum binding of PpL to IgG.

100 μl human IgG, dilution 1.250, was added to each well and the plate was then incubated for 45 minutes. The plate was washed again with PBST and 200 μl goat anti-human Fc specific IgG-HRP (horse radish peroxidase) diluted 1.1250 was added to each well and the plate was incubated for a further 45 minutes. Following a further three washes with PBST, the substrate was added (0.4 mg/ml O-phenylenediamine, 0.01% $H_2O_2$ in citrate/phosphate buffer).

Determining the Kd for the Interaction between Y53F PpL and IgG

The Kd for the complex at equilibrium between IgG and Y53F PpL or Y53F Y64W PpL was established by competitive ELISA to yield Kds of 3.2±0.5 μM and 3.32±0.5 μM respectively at pH 8.0. As noted above, the Kd previously determined for PpL was 112±20 nM. The removal of the hydroxyl group had caused an increase in Kd of about 25±5 fold, suggesting that the group normally plays an important role in the stability of the complex. This change in the Kd enables the complex to be dissociated under less harsh conditions than wild type.

The Effect of pH

The effect of pH was studied under equilibrium and pre-equilibrium conditions. The complexes of both proteins (Y64W PpL and Y53F Y64W PpL) with κ-chain were most stable at pH 8.0 when measured under equilibrium conditions.

The effect of pH on the rate of dissociation was also examined. The Y64W PpL κ-chain complex dissociates most quickly at pH 9.0, while the Y53F $Y_{64}$W PpL κ-chain complex dissociated fastest at pH 5.0. This suggested that an ionisable group caused an increased rate of dissociation of the Y64W PpL κ-chain complex at pH 9.0, and that this group was no longer affecting the rate of dissociation of the Y53F Y64W PpL κ-chain complex.

Stability of N64W PpL and Y53F Y64W PpL

The stability of the proteins was determined by studying the change in molar ellipticity at 225 nm, with increasing temperature. The results showed that the Tm of PpL is 72.4±0.5° C. Y64W PpL is 73.8±0.6° C. and Y53F Y64W PDL is 73.2±0.4° C. This indicated that the stability of the proteins was unaffected by the mutagenesis experiments, and that therefore the reduction in affinity observed with the Y53F constructs was not due to the instability of the proteins.

Affinity Chromatography

Previous studies of coupled protein L have been carried out. However the elution conditions required were harsh, involving the use of glycine-HCl buffer at pH 2.0. Previous studies on PpL required 0.5M acetic acid for elution of the κ-chain. Therefore the lower affinity of Y53F PpL with κ-chain could allow the purification of immunoglobulin to occur under more mild conditions.

PpL, Y64W PpL and Y53F PpL were coupled to triazine activated agarose following the manufacturers guidelines (Affinity Chromatography Ltd, Cambridge United Kingdom). The columns were equilibrated in 20 mM-phosphate, pH8. 1 mg human κ-chain was added to the three affinity columns and each column was washed in the 20 mM phosphate buffer, pH8, until all unbound protein had been removed. The bound proteins were eluted either with 50 mM sodium acetate or carbonate buffers of changing pH, or increasing KCl concentrations. The elution conditions of PpL, Y64W PpL and Y53F PpL can be found in Table 2.

TABLE 2

| Protein L | Elution conditions required to dissociate the κ-chain from a Protein L column | | |
|---|---|---|---|
| | increased pH | decreased pH | increase KCl(M) |
| PpL | 10.2 | 1.96 | 0.95 |
| Y64W PpL | 10.12 | 2.03 | 0.96 |
| Y53F PpL | 9.6 | 3.2 | 0.75 |

It can be seen that the elution conditions required to elute κ-chains from the Y53F PpL affinity column were not as harsh as those needed for the PpL or Y64W PpL column.

The substitution of the tyrosine residue at position 53 by a phenylalanine residue had the effect of reducing the affinity of the protein L κ-chain complex by a factor of 27. The substitution of the tyrosine side chain with a phenylalanine retained the aromatic nature of the side chain although increased its hydrophobic nature. The Tm of the proteins indicated that the stability of the proteins was unchanged in spite of the substitutions made.

The rate of dissociation of the Y53F PpL κ-chain complex was affected by pH and dissociated faster at lower pH values. This was not the case for Y64W PpL, which dissociated fastest at pH9.

Protein L has been shown to purify antibodies, although the elution of bound proteins has to be carried out under harsh conditions. Due to the decreased binding affinity of Y53F PpL, it was proposed that purification could occur under with milder conditions. Affinity chromatographic studies have revealed that Y53F PpL can effectively separate mixed λ-chain and κ-chain and release the bound κ-chain with less harsh conditions than PpL, resulting in a particularly effective immunological tool.

Further Studies on Effect of Amino Acid Substitutions

Additional studies were carried out to study the effect of amino acid substitutions on binding affinity for κ-chain Kd values were determined at pH 8. The results are set out in Table 3 below. A "✓" denotes that the specified mutation was introduced into PpL, Y64W PpL or F39W PpL.

TABLE 3

| Mutation | PpL | Y64W PpL | F39W PpL | Kd |
|---|---|---|---|---|
| F39W | ✓ | | | 160 nM |
| Q35E | | ✓ | ✓ | 300 nM |
| Q35C | No expression | | | |
| E38Q | No expression | | | |
| F39H | ✓ | ✓ | | 1 μM |
| Y53H | | | ✓ | 500 nM |
| Y53F | ✓ | ✓ | | 1.7 μM |
| Y53W | ✓ | | | |
| L57D | | ✓ | | 2 μM |
| L57H | ✓ | ✓ | | 6 μM |
| L57K | In M13 | | | |
| K59G | No expression | | | |
| 59G60 | ✓ | | | |
| N76D | | | ✓ | 400 nM |
| K40I | In M13 | | | |

Specific substitutions at positions 39, 53 and 57 and an insertion between positions 59 and 60 markedly affected the binding affinity. Some of the other substitutions did not result in expression of any polypeptide, potentially due to instability of the mutated polypeptide.

Characterization of L57H PpL

One mutant describe above L57H PpL, has been characterized by a number of techniques including ELISA, stopped-flow fluorescence spectroscopy, isothermal titration calorimetery (ITC) and affinity chromatography. PpL contains no native tryptophans, so in order to carry out stopped flow experiments on L57H a second mutation, a tryptophan reporter group (Y64W) was introduced. The Y64W PpL has binding properties similar to those of Wt PpL.

Competitive ELISA

Competitive ELISA experiments as described above competing L57H PpL with immobilized Wt PpL gave a Kd value for the binding of L57H PpL to human IgG to be ≈4.2 $\mu$M. This shows a significantly lower binding affinity than Wt PpL which has a Kd of 160 nM for the same complex.

Stopped Flow Fluorescence

All stopped flow measurements were made using an Applied Photophysics spectrophotometer, using a 1:1 mixing ratio. Solutions were made up in 20 mM $PO_4$ buffer unless otherwise stated. An excitation wavelength of 280 nm was used and fluorescence emissions above 335 nm were selected using a suitable cut off filter. FIG. 1 shows the binding of L57HY64W to kappa chain to be a biphasic process. The initial rapid phase is due to the formation of an encounter complex, followed by what is believed to be a slower conformational change, resulting in the formation of the high affinity complex.

Figure 2:
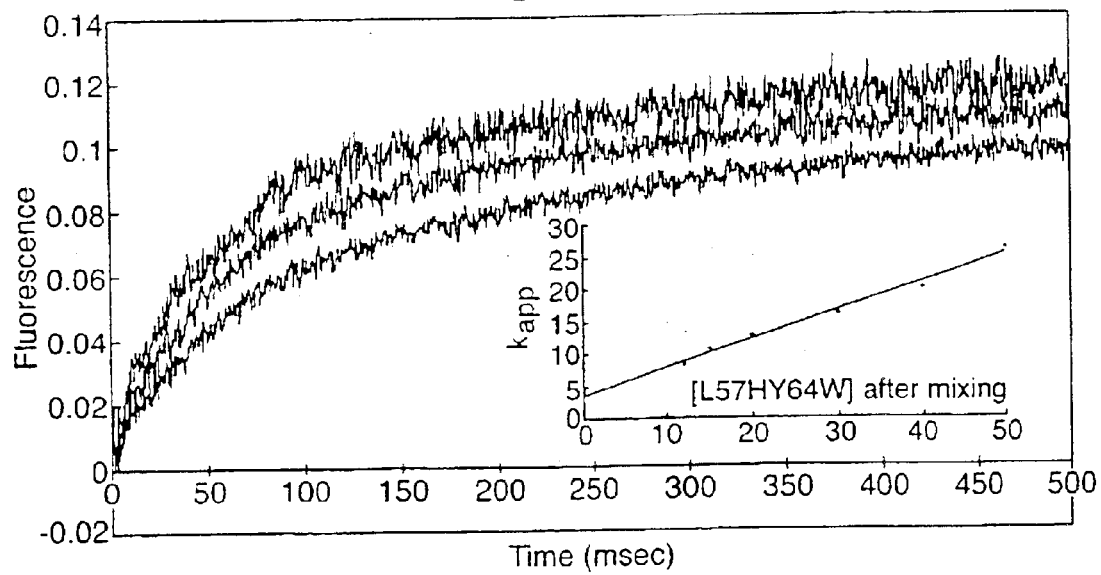
FIG. 2 Stopped flow fluorescence following complex formation over 0.5 seconds when 4 μM kappa is mixed in a 1:1 volume ratio with 24 μM (—), 60 μM (- - - -) and 80 μM ( . . . ) L57HY64W. Inset, the dependence of $k_{app}$ on L57HY64W concentration. From this second plot it is possible to determine the rates $k_{on}$ and $k_{off}$ for the formation of the pre-equilibrium complex.

In order to measure $k_1$ and $k_{-1}$ the apparent rate of reaction ($k_{app}$) is measured using about 4 $\mu$M kappa chain and several different concentrations of L57HY64W between 20 and 100 $\mu$M. The values of $k_1$ and $k_{-1}$ are determined from the slope and intercept of the curve in the inset to FIG. 2.

Stopped-flow studies on the binding of L57HY64W to kappa chain have shown the pre-equilibrium Kd to be ≈6.8 $\mu$M and the equilibrium Kd to be ≈5.4 $\mu$M. The pre-equilibrium Kd is only approximately 2 fold higher than that found for Y64W PpL, where as the equilibrium Kd is approximately 30 fold greater than that of Y64W PpL, indicating the main effect of the L57H mutation is on the rate of the conformational change not the formation of the encounter complex.

Isothermal Titration Calorimetery

Figure 3:
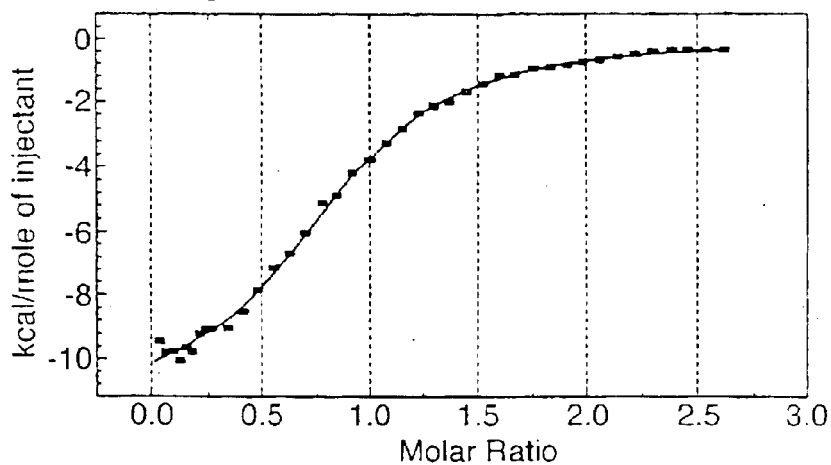
FIG. 3. ITC titration of 800 μM L57H PpL into 40 μM kappa light chain. The titration gives the Kd of L57H PpL binding to kappa to be 5.2 μM +/− 0.4 μM.

All ITC titrations were carried out at 25° C. using a Microcal VP-ITC microcalorimeter. The Cell was filled with kappa light chain in 20 mM PO4 buffer pH 8.0, into which L57H PpL in identical buffer was titrated. The curve in FIG. 3 yields an equilibrium Kd of 5.2 $\mu$M in agreement with stopped-flow studies.

Near and Far UV Circular Dichroism Spectroscopy

Figure 4:
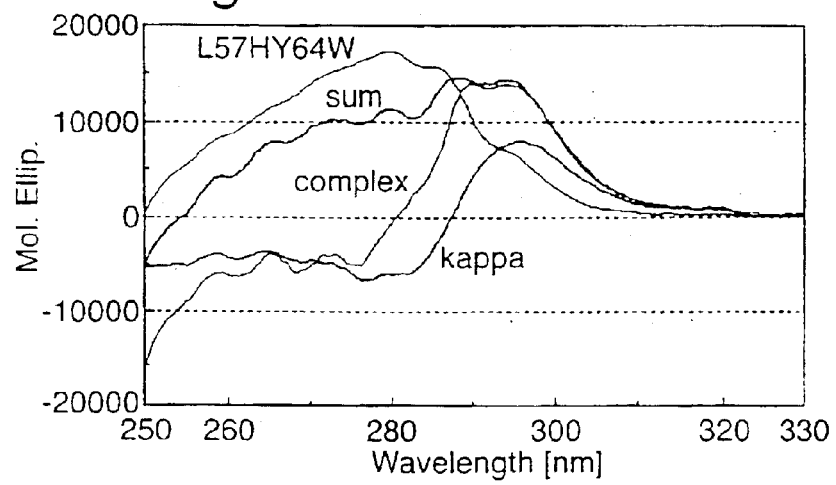
FIG. 4. Near UV spectra of L57HY64W (- - - -), kappa (- - - -),L57H Kappa complex ( . . . ) and the theoretical sum of kappa +L57HY64W (—).
Figure 5:
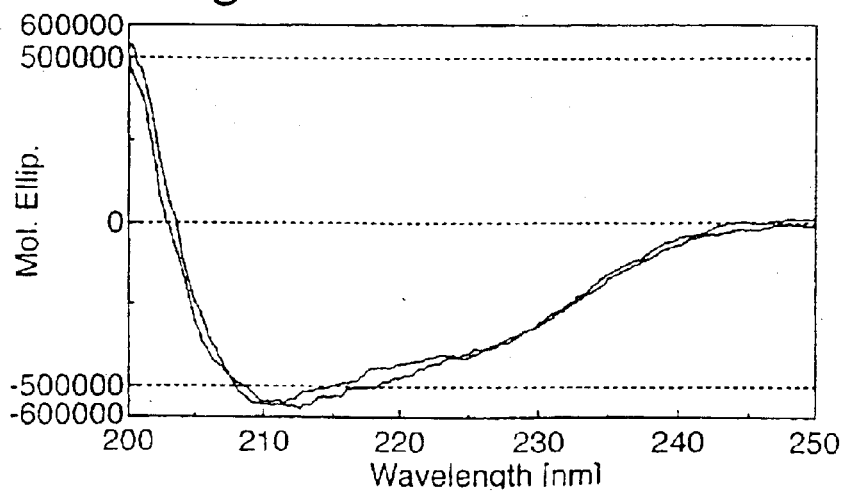
FIG. 5. Far UV spectra of L57H ( . . . ) and Wt Ppl (- - - -).

All CD measurements were made using a JASCO J720. Near UV spectra were taken in the range 250 to 320 nm, using a scan speed of 100 nm/min, a path length of 1 cm, slit widths of 500 $\mu$M, response time of 4 seconds a band width of 1 nm. and a resolution of 0.2 nm. Each scan shown is the average of 16 accumulations. The near UV scan shows a significant decrease in ellipticity upon the formation of the complex (FIG. 4). This is due to a change in the environment of tyrosine 53. There is very little difference in the far UV spectra of Wt and L57H PpL (FIG. 5), showing the decreased affinity of L57H PpL for kappa is not due to a changed secondary structure.

Example 2

Construction of a 2 Domain Peptide

DNA Constructs

The synthetic gene, termed $PpL_c$, was constructed using 8 oligonucleotides of lengths 59–66 bases and two linker oligonucleotides of 50 bp each. These oligonucleotides had been designed to cover the whole of a single immunoglobulin-binding domain of protein L. They were also designed with overlapping cohesive sticky ends and various internal and terminal restriction enzyme sites to facilitate cloning. The internal 5' ends of these oligonucleotides were phosphorylated using T4 polynucleotide kinase. Complementary oligonucleotides were then annealed by heating each pair separately to 85° C. followed by cooling to room temperature over an hour. The pair of linker oligonucleotides were annealed and then diluted 1:10 v/v in sterile distilled water and stored at −20° C. until needed. Annealed pairs each had a 6 bp cohesive overlap with the neighbouring pair of oligonucleotides and the four pairs were ligated together using T4 ligase at 14° C. overnight. The products of this ligation were run on an agarose gel and the product corresponding to a ligation of all four of the annealed pairs (the 240 bp band) was separated from the smaller ligated products and isolated using a Qiagen gel extraction kit. This DNA was then ligated into a pKK233-2 plasmid which had been digested with Nco I and HinDIII, the sticky ends engineered onto the 5' and 3' ends of the synthetic construct. Sequencing was used to confirm that a plasmid containing a single domain of protein L was produced.

Construction of the Two Domain Gene

Figure 6:
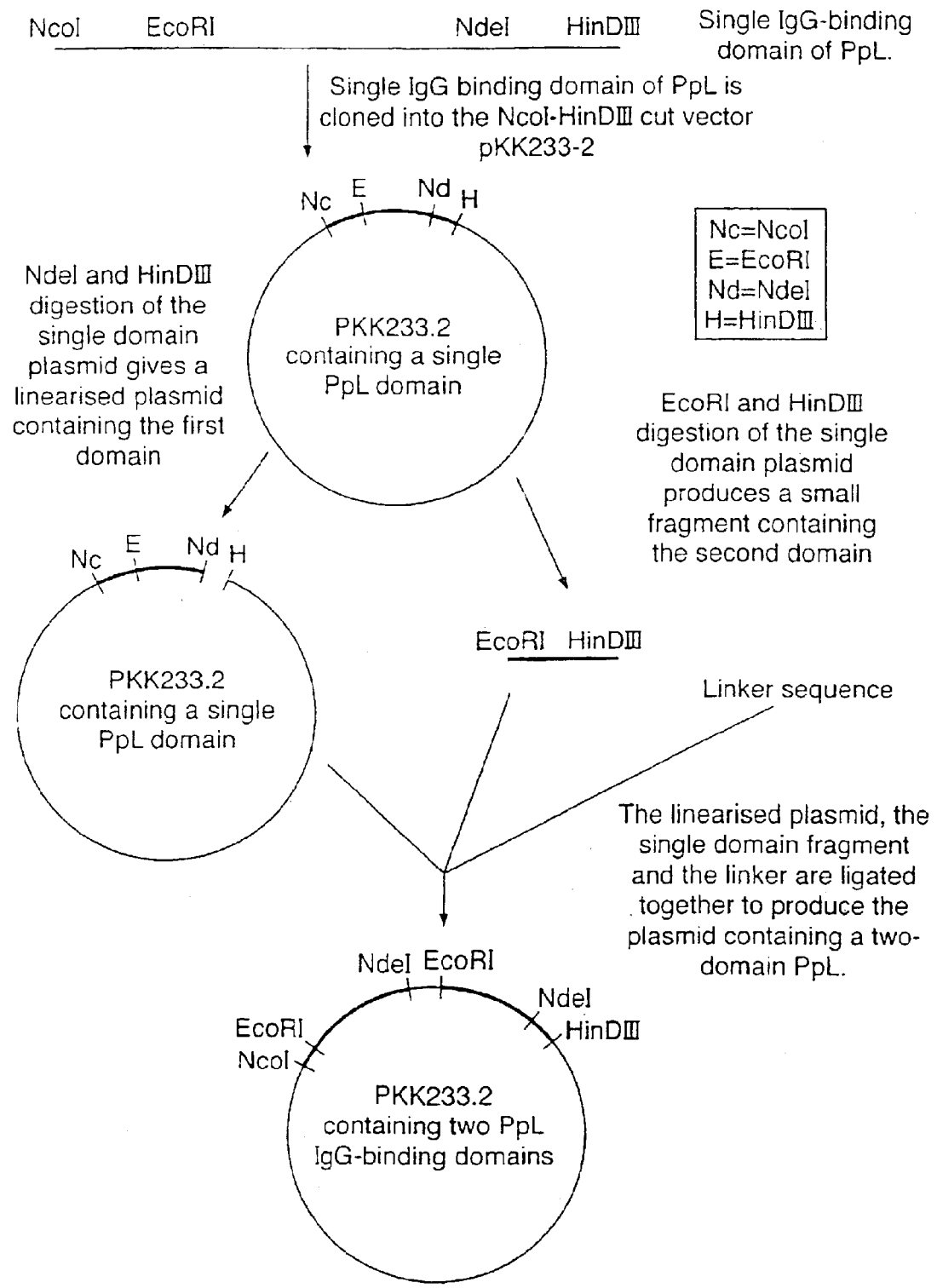
FIG. 6. Strategy used to create a double domain polypeptide, from the cloned single domain fragment.

The two-domain construct was made by isolating different fragments from the above $PpL_c$ single domain. FIG. 6 shows the strategy used. The single domain plasmid was partially digested with NdeI and the DNA fragment corresponding to the linearised plasmid was isolated from an agarose gel. This DNA was then further digested with HinDIII and again the fragment corresponding to the linearised plasmid was extracted from an agarose gel. The initial partial digestion was necessary as the plasmid pKK233-2 contained a NdeI site in addition to the one present in the single PpL DNA synthetic gene. These digestions gave a linearised plasmid with a single PpL IgG-binding domain followed by a NdeI sticky end, with a HindIII cohesive site at the other end of the plasmid. In a separate reaction the single domain PpL plasmid was digested with EcoRI and HindIII to give a 240 bp fragment which was purified as before. A ligation reaction was set up containing the linearised NdeI-HinDIII plasmid, the EcoRI-HinDIII 240 bp fragment and the synthetic linker prepared earlier. This reaction was performed using T4 DNA ligase at 14° C. overnight. This DNA was transformed into JM103 *E. coli* bacteria and a number of colonies were picked and grown overnight. DNA was prepared from these cultures using a Qiagen mini prep kit and this DNA was digested with NcoI and HinDIII to check for the presence of a 500 bp band corresponding to a double domain PpL gene. DNA sequencing confirmed the presence of a successfully ligated PpL double domain gene (termed PpL2Ala)

Mutagenesis

The double domain PpL gene was mutated using a PCR mutagenesis method. Two primers were designed that annealed to the same sequence on opposite strands of the plasmid and contained the desired mutation close, to the middle. The primers were 30–45 bp in length with a melting temperature around 80° C. The primers also had a minimum GC content of 40%, terminated in a G or C, and were HPLC purified. The primers (with the mutations shown in bold) for the A2N mutation were 5' CAG GAA ACA GAC CAT GAA CAT TAA ATT TGC TGG (SEQ ID NO: 31) with its complement and for F39W 5' CAA ACA GCA GAA TGG AAA GGA ACA TTT GAA GAA GC (SEQ ID NO: 32) and its complement. The mutagenesis reactions all contained 125 ng of each primer, 0.5 mM dNTPs (0.125 mM each dNTP), 1× reaction buffer (10×buffer contains 100 mMKCl, 60mM $(NH_4)_2SO_4$, 200 mM Tris-HCl (pH 8), 20 mM $MgCl_2$, 1% Triton X-100, 100 μg/ml nuclease free BSA). The amount of dsDNA template was varied from 5 to 50 ng per reaction and 2.5U. cloned Pfu polymerase(Stratagene) was added to each. After overlaying with mineral oil the reactions were initially heated to 95° C. for 5 minutes, followed by 16 cycles of 95° C. for 30 seconds, 58° C. for 1 minute and 68° C. for 12 minutes. Dpn I enzyme (10 units) was then added to each reaction and, after thorough mixing, the reactions were incubated at 37° C. for 4 hours. 2 μl from each reaction was then used to transform competent XL1-BLUE *E. Coil* bacteria which were then grown on LB-ampicillin plates. Colonies were picked and DNA prepared. Sequencing was used to check for the presence of the desired mutation.

Protein Induction and Preparation

Double domain PpL plasmid was initially transformed into JM103 *E. coli* bacteria. Single colonies were then used to innoculate 5 ml LB cultures containing, 50 μg/ml ampicillin, and these cultures were grown at 37° C. for 16 hours. A 2 liter flask containing 500 mls LB media with 50 μg/ml ampicillin was inoculated with 1 ml of this overnight culture and grown at 37° C. until an optical density of $A_{600}$ 0.6–0.9 was reached. The expression of PpL was then induced by the addition of 0.6 mM IPTG. The cultures were grown for an additional 4 hours post induction and the cells were then spun down and stored at −20° C. To purify the protein the cells were resuspended in approximately 30 mls of sonication buffer. Lysozyme and DNAse I were added to a final concentration of 0.1 mg/ml each and PMSF to 2 mM. After a 20 minute incubation at room temperature, the cells were disrupted by sonication. Cell debris was removed by centrifugation and the proteins in solution were heated to 70° C. for 40 minutes in a water bath. The denatured proteins were removed by centrifugation and the remaining proteins in solution were made up to 100 mls with 20 mM Tris-HCl pH 8, 2M NaCl. This was loaded onto a column of Butyl toyopearl 650M matrix. An initial wash of 20 mM Tris-HCl pH 8.0, 2M NaCl was performed for 90 minutes followed by a linear gradient to 20 mM Tris-HCl over 400 minutes. The protein was loaded and the washes performed at a speed of 1.5 mls/min and fractions were collected from the start to the end of the gradient (5 minutes/tube). Spectral analysis at $A_{280}$ revealed the presence of protein. SDS-PAGE was carried out and showed the location of purified double domain PpL. Protein concentration was estimated by the bicinchoninic acid protein assay of Smith et al (1985) (Sigma).

Enzyme-linked Immunosorbent Assay (ELISA)

The IgG or kappa chain binding activity of a protein solution was quantified u using a micro ELISA technique. Serial dilutions of the protein in 0.05M carbonate/bicarbonate coating buffer, pH 9 (200 μl volume) were used to coat the wells of a microtitre plate at either room temperature overnight or at 37° C. for 2 hours. Wells were then washed three times with PBS containing 0.1% tween before incubation with 200 μl human IgG or human kappa light chain at room temperature for 45 minutes. Wells were then washed 3× again with PBS-Tween before a 45 minute incubation with goat anti-human anti-IgG-HRP conjugate at room temperature. An additional 3 washes were then performed with PBS-Tween and 200 μl of the substrate solution (0.35 mg/ml o-phenylenediamine, 0.1% v/v $H_2O_2$ in 0.1M cirate/phosphate buffer, pH 5) was added to each well. The reaction was stopped after about 30 minutes by the addition of 50 μl 12.5% $H_2SO_4$ and the absorbance read at 495 nm using a Dynatech MR5000 automated plate reader. This ELISA was also carried out using single kappa chain and anti-kappa-HRP conjugate.

Competitive ELISA

Competitive ELISAs were used to calculate the $K_d$ for the PpL2Asn for human IgG and human kappa chain. The wells of a microtitre plate (excluding row 1 which was left as a blank control) were coated with 4 μg of wt PpL in 200 μl of sodium/carbonate buffer, pH 9.5 at room temperature overnight. Three washes with PBS-T (phosphate buffer saline containing 0.1% (v/v) tween 20) were performed and 150 μl PBS-T added to each well. The PpL2Asn protein (100 μl of 0.08 mg/ml) was then added to row 2 and serially diluted across the plate, leaving row 12 with no competing protein as a control for maximal binding of PpL to IgG. 100 μl human IgG containing kappa chain (6 mg/ml) was diluted 1:250 v/v with PBS-T and 200 μl added to each well and the plate incubated for 45 minutes at room temperature before again being washed three times with PBS-T. The goat anti-human Fc specific IgG-HRP (horse radish peroxidase) conjugate (200 μl of a 1:675 v/v PBS-T dilution) was then added to each well and incubated for a further 45 minutes at room temperature. The washes, substrate addition and reading of the plate was carried out as above The concentration of the competitor protein that decreased the absorbance at 495 nm by 50% was used to estimate the $K_d$. This process was also repeated using single human kappa light chain and anti-human kappa light chain-HRP conjugate (Sigma).

Competitive Fluorescence Titrations

Competitive titrations were carried out at 18° C. using, a 2 ml solution of 0.75 μM kappa chain in 20 mM potassium phosphate buffer at pH 8. Aliquots of a 100 μM stock solution of F39W were added to the kappa solutions both in the presence of the competitor protein PpL2Asn (5 μM) and in the absence. The excitation wavelength was 280 nm and the emission wavelength 325 nm. Each titration was repeated three times and the fluorescence intensities corrected for the inner filter effect by the equation.

$$F_{corr} = F_{obs} \times \exp^{(0.5\ Aex + 0.5\ Acm)}$$

where $F_{corr}$ is the corrected fluorescence intensity, $F_{obs}$ is the observed fluorescence, $A_{ec}$ is the absorbance at the excitation wavelength and $A_{cm}$ is the absorbance at the emission wavelength measured in 1 cm light path cells. The titration curves were analysed by fitting the data to the equation.

$$\frac{K_d}{(1-\alpha)} = \frac{[P]o}{\alpha} - [B]o$$

where $K_d$ is the dissociation constant, α is the fractional saturation of PpL sites on the kappa chain, [P]o is the total concentration of PpL and [B]o is the total molarity of binding sites available for PpL. This allowed the $K_d$ for F39W binding to be calculated and the $K_{app}$ for the F39W binding in the presence of the PpL2Asn competitor. The $K_i$ (dissociation constant of the competitor) was then calculated from the equation.

$$K_{d\ app} = Kd\ (1+i/K_1)$$

where $K_{d\ app}$ is the apparent dissociation constant for F39W in the presence of the competitor, $K_d$ is the dissociation constant for F39W calculated in the absence of any inhibition, i is the concentration of the inhibitor and $K_1$ is the unknown dissociation constant for the inhibitor.

Ouchterlony Plate

An Ouchterlony plate was used to establish if the double domain was capable to precipitating IgG as shown by four domain Protein L or Protein A. A 0.5% agarose gel was poured in a 10 cm petri dish and allowed to set. Small wells were then made in the gel approximately 5–10 mm apart. A cross shape was used with 1 central well and four wells around this IgG or kappa chain were pipetted into the central well and WT single domain Protein L, PpL2Asn. Four-domain Protein L and Protein A were placed separately in the surrounding wells. The plate was wrapped in cling film and incubated at room temperature overnight. The next day the plate was examined for the presence of a white mark between any of the wells as this indicated the formation of a precipitate.

Results

Design and Cloning of the Double Domain Gene Construct

The double domain gene was constructed from a total of 10 oligonucleotides ranging from 50 bp to 65 bp in size, to make up a complete single immunoglobulin binding domain of PpL. This complete single domain was constructed by annealing the oligos into pairs, ligating them all together and then subcloning this 240 bp product into linearised pKK233-2 as described in materials and methods. Restriction endonuclease digestion yielded products that were then ligated together such that two immunoglobulin-binding domains joined by a linker region were then present in the pKK233-2 vector.

The oligonucleotides used in the construction of the gene were designed from the single domain PpL strain 3316. The sequence of each of the domains in the double domain construct is almost identical to that which is found in the single domain clone, with just a few differences which were necessary or desirable to introduce. It was necessary to have suitable enzyme sites at the 5' and 3' ends of the gene for subcloning into a suitable expression vector NcoI was positioned at the 5' end and HinDIII at the 3' end. The HinDIII site did not require any sequence alterations but the NcoI site did. Residue 2 is an asparagine in WT single domain PpL but for the two domain construct was altered to an alanine so that the sequence was correct for a Nco I site (CCATGG). The original sequence was CC ATG AAC with methionine followed by asparagine but this was altered to CC ATG GCA to accommodate the Nco I site and so changing the second residue to alanine. Two internal restriction enzyme sites were eliminated so that they did not interfere with the cloning strategy. An internal HinDIII site was removed by altering residue 50 from GCT to GCA (a silent mutation). An internal EcoRI site was also eliminated by another silent mutation at position 39 where TTC was changed to TTT. An insertion of an EcoR I site at position 10 caused a change from a threonine (ACA) to a phenylalanine (TTC). It was thought that most of these changes would not cause considerable differences to the properties of the protein. The silent mutations did not alter any amino acids and the codon usage in E. coli was considered to try to minimise any affects that different codons may have on translational levels. The changes at positions 2 and 10 do not occur within the actual PpL domain as the first 20 amino acids are a non-functional region that allows high expression of the cloned gene fragment. The other changes that were introduced were advantageous for some applications. At position 53 in both domains the tyrosine residue was altered to a phenylalanine. A cysteine residue was included at position 79 of the second domain only (residue 161) so that thiol immobilisation could be achieved if required. Overall the differences in the double domain compared to the wt single domain PpL are N2A, T10F, Y53F, T92F, Y135F, F161C.

Protein Expression and Binding Interactions

Expression of the gene construct in E. coli cells revealed a band at approximately 18 KDa the size expected, but unfortunately the expression was low. This weak expression may have been due to the alteration of the second residue from an asparagine to an alanine. It was therefore decided to revert this second residue to asparagine by PCR mutagenesis, as described. Sequencing confirmed the presence of the desired residue and SDS-page analysis showed that expression levels of this mutated protein were better than that of the original double domain which contained the alanine at position 2. This protein was used for all subsequent experiments.

The ELISA results showed that the PpL2Asn binds strongly to IgG The $K_d$ estimated from the ELISA results was 60 nM, a value in the same order as that obtained for wild type single domain PpL. The Y53F single domain PpL binds to IgG with a $K_d$ of approximately 2 $\mu$M, so the two domain protein has considerably stronger binding to IgG than that expected from the mutant single domain. The binding of the PpL2Asn to single kappa chain was found by ELISA to be 4 $\mu$M, approximately double the value for Y53F single domain. This result is backed up by data from Isothermal titration calorimeter studies that also showed that the $K_d$ for the Y53F PpL2Asn is about 4 $\mu$M. Fluorescence studies were also carried out. Direct titrations were not possible as the PpL2Asn does not contain any reporter fluorescent residues so competitive titrations were carried out. F39W single domain PpL titrations into kappa chain were performed in the presence and absence of the PpL2Asn. The double domain acted as a competitor for kappa chain and so inhibited the normal titration curve seen with F39W titrations into kappa chain. The $K_d$ for F39W binding to kappa chain was found to be 161 nM±34 nM. The $K_{dapp}$ for F39W binding kappa chain in the presence of 5 $\mu$M competing PpL2Asn was found to be 310 nM±46.4 nM. The level of inhibition allowed the $K_d$ of the double domain to be calculated and was found to be approximately 5.5 $\mu$M.

The Ouchterlony plate showed that both Protein A and the four-domain PpL gave a white precipitate when in contact with the IgG. This was not observed for Protein A or four domain PpL in contact with single kappa chain, indicating that one of the molecules is univalent (kappa chain). The single domain PpL and PpL2Asn do not give a precipitate when in contact with IgG or single kappa chains under the same conditions. This shows that neither of these molecules were able to bind to more than one IgG molecule at a time.

These results indicate that the binding of the double domain Y53F protein to IgG is relatively strong but the binding to kappa chain is weaker, and more equivalent to that of the single domain PpL.

The much higher affinity of the Y53F domain to IgG (60 nM as opposed to 2 $\mu$M) is also unexpected. It is possible that the higher binding is caused by the interaction of both of the PpL domains with both of the kappa chains of a single IgG molecule. This type of complex would be expected to have a more stable structure than a single interaction. This theory is backed up by the Ouchterlony plate results. If the PpL2Asn were able to bind to two kappa chains on different IgG molecules then this would also be expected to give a precipitate. No precipitate was observed for either the WT single domain PpL or the PpL2Asn showing that neither of these are capable of binding to more than a single IgG molecule. This, coupled with the ELISA result showing PpL2Asn binding tightly to IgG, suggests that the PpL2Asn molecule binds to both kappa chains of a single IgG molecule but it is not able to bind to two kappa chains on separate IgG molecules.

What is claimed is:

1. A method of isolating an immunogloblin comprising providing a solid support having bound thereto a protein and contacting a sample containing the imniunoglobulin with the support, wherein the protein bound to the support is an immunoglobulin light chain binding protein which comprises:

(a) the amino acid sequence of SEQ ID NO: 1 modified by an amino acid substitution at one or more of positions 39, 53 and 57 and/or by an amino acid insertion between positions 59 and 60, such that the dissociation constant (Kd) of the protein with respect to human immunoglobulin kappa chain is 400 nM or more at pH 8, or (b) the amino acid sequence of a corresponding immunoglobulin light chain binding domain modified by an amino acid substitution at one or more of the positions equivalent to positions 39, 53 and 57 of SEQ ID NO: 1 and/or by an amino acid insertion between positions equivalent to positions 59 and 60 of SEQ ID NO: 1, such that the dissociation constant (Kd) of the protein with respect to human immunoglobulin kappa chain is 400 nM or more at pH 8, or (c) the amino acid sequence of a fragment of (a) or (b) which contains at least one said substitution and/or insertion, such that the dissociation constant (Kd) of the protein with respect to human immunoglobulin kappa chain is 400 uM or more at pH8.

2. A method according to claim 1 wherein the immunoglobulin light chain binding protein comprises the amino acid sequence of SEQ ID NO: 1 having a histidine residue at position 39.

3. A method according to claim 1 wherein the immunoglobulin light chain binding protein comprises a phenylalamine residue at position 53 and/or an aspartic acid or histidine residue at position 57.

4. A method according to 3 wherein the immunoglobulin light chain binding protein further comprises a tryptophan at position 39.

5. A method according to claim 1 further comprising extracting the immunoglobulin from the support.

* * * * *